(12) United States Patent
Takahashi et al.

(10) Patent No.: US 11,083,533 B2
(45) Date of Patent: Aug. 10, 2021

(54) MANIPULATOR SYSTEM AND OPERATING METHOD THEREOF

(71) Applicant: OLYMPUS CORPORATION, Tokyo (JP)

(72) Inventors: Keigo Takahashi, Tokyo (JP); Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 157 days.

(21) Appl. No.: 16/011,163

(22) Filed: Jun. 18, 2018

(65) Prior Publication Data

US 2018/0296288 A1     Oct. 18, 2018

Related U.S. Application Data

(63) Continuation of application No. PCT/JP2016/055717, filed on Feb. 25, 2016.

(51) Int. Cl.
*A61B 34/00* (2016.01)
*A61B 90/00* (2016.01)
(Continued)

(52) U.S. Cl.
CPC .............. *A61B 34/70* (2016.02); *A61B 34/37* (2016.02); *A61B 34/71* (2016.02); *A61B 34/74* (2016.02);
(Continued)

(58) Field of Classification Search
CPC ......... A61B 34/30; A61B 34/32; A61B 34/37; A61B 34/70; A61B 34/71; A61B 34/74;
(Continued)

(56) References Cited

U.S. PATENT DOCUMENTS

| 7,974,681 B2 | 7/2011 | Wallace et al. |
| 2003/0033024 A1 | 2/2003 | Sunaoshi |

(Continued)

FOREIGN PATENT DOCUMENTS

| EP | 1728462 A2 | 12/2006 |
| EP | 2014218 A2 | 1/2009 |

(Continued)

OTHER PUBLICATIONS

Supplementary Partial European Search Report for European Application No. 16891497, dated Aug. 28, 2019.
(Continued)

*Primary Examiner* — Tuan V Nguyen
(74) *Attorney, Agent, or Firm* — The Dobrusin Law Firm, P.C.

(57) ABSTRACT

A manipulator system is provided with: a manipulator including an elongated flexible portion, a movable portion provided at a distal end thereof, and a driving portion that is provided at a proximal end of the flexible portion and that drives the movable portion; an inserted portion that includes a channel through which the manipulator is made to pass and that possesses flexibility; a reciprocating portion that moves the driving portion forward and backward in a longitudinal direction of the flexible portion; a movable-portion-state identifying portion that identifies a state of the movable portion; a restricting portion that, when the movable portion is identified to be in a protruded state, restricts the driving portion from being moved backward any farther; and a restriction releasing portion that, when the movable portion is identified to be in a retractable state, releases the restriction.

11 Claims, 19 Drawing Sheets

(51) Int. Cl.
  *B25J 13/02* (2006.01)
  *A61B 34/37* (2016.01)
  *B25J 9/00* (2006.01)
  *A61B 34/30* (2016.01)
  *A61B 18/14* (2006.01)

(52) U.S. Cl.
  CPC ............. *B25J 9/0009* (2013.01); *A61B 18/14* (2013.01); *A61B 2034/301* (2016.02); *A61B 2090/3937* (2016.02); *B25J 9/0096* (2013.01)

(58) Field of Classification Search
  CPC ............ A61B 1/00066; A61B 1/00087; A61B 1/00105; A61B 1/00133; A61B 1/00149; A61B 17/29; A61B 17/00234; B25J 9/0009
  See application file for complete search history.

(56) References Cited

U.S. PATENT DOCUMENTS

| | | | |
|---|---|---|---|
| 2003/0135203 A1* | 7/2003 | Wang | G05B 15/02 606/1 |
| 2006/0100610 A1 | 5/2006 | Wallace et al. | |
| 2006/0276784 A1 | 12/2006 | Miyajima et al. | |
| 2007/0043338 A1 | 2/2007 | Moll et al. | |
| 2007/0088354 A1 | 4/2007 | Sugita | |
| 2007/0135803 A1 | 6/2007 | Belson | |
| 2007/0250074 A1 | 10/2007 | Brock et al. | |
| 2008/0183193 A1 | 7/2008 | Omori et al. | |
| 2008/0188868 A1 | 8/2008 | Weitzner et al. | |
| 2008/0188869 A1 | 8/2008 | Weitzner et al. | |
| 2008/0188871 A1 | 8/2008 | Smith | |
| 2008/0188890 A1 | 8/2008 | Weitzner et al. | |
| 2008/0193260 A1 | 8/2008 | Yokokohji et al. | |
| 2008/0221391 A1 | 9/2008 | Weitzner et al. | |
| 2008/0243176 A1 | 10/2008 | Weitzner et al. | |
| 2009/0018390 A1 | 1/2009 | Honda et al. | |
| 2009/0275798 A1 | 11/2009 | Naito | |
| 2009/0326319 A1 | 12/2009 | Takahashi et al. | |
| 2010/0331856 A1 | 12/2010 | Carlson et al. | |
| 2012/0004502 A1 | 1/2012 | Weitzner et al. | |
| 2012/0143353 A1 | 7/2012 | Kishi | |
| 2012/0191247 A1 | 7/2012 | Kishi | |
| 2014/0005683 A1 | 1/2014 | Stand et al. | |
| 2014/0148817 A1* | 5/2014 | Hasegawa | A61B 17/29 606/130 |
| 2014/0246471 A1 | 9/2014 | Jaworek et al. | |
| 2014/0246472 A1 | 9/2014 | Kimsey et al. | |
| 2014/0246473 A1 | 9/2014 | Auld | |
| 2014/0246474 A1 | 9/2014 | Hall et al. | |
| 2014/0246475 A1 | 9/2014 | Hall et al. | |
| 2014/0246476 A1 | 9/2014 | Hall et al. | |
| 2014/0246477 A1 | 9/2014 | Koch, Jr. et al. | |
| 2014/0246478 A1 | 9/2014 | Barber et al. | |
| 2014/0246479 A1 | 9/2014 | Barber et al. | |
| 2014/0249557 A1 | 9/2014 | Koch, Jr. et al. | |
| 2015/0238180 A1 | 8/2015 | Weitzner et al. | |
| 2015/0313449 A1 | 11/2015 | Stand et al. | |
| 2016/0089007 A1 | 3/2016 | Weitzner et al. | |
| 2016/0228113 A1 | 8/2016 | Weitzner et al. | |
| 2016/0324589 A1 | 11/2016 | Ogawa et al. | |
| 2017/0007345 A1 | 1/2017 | Smith et al. | |
| 2017/0007347 A1 | 1/2017 | Jawirek et al. | |
| 2017/0265953 A1 | 9/2017 | Fenech et al. | |
| 2018/0360551 A1 | 12/2018 | Ogawa et al. | |
| 2019/0231466 A1 | 8/2019 | Weitzner et al. | |

FOREIGN PATENT DOCUMENTS

| | | |
|---|---|---|
| EP | 2113187 A1 | 11/2009 |
| EP | 2116174 A1 | 11/2009 |
| EP | 2772209 A1 | 9/2011 |
| EP | 2617530 A1 | 7/2013 |
| EP | 2639018 A1 | 9/2013 |
| EP | 2772196 A2 | 9/2014 |
| EP | 2772204 A2 | 9/2014 |
| EP | 2772205 A1 | 9/2014 |
| EP | 2772206 A2 | 9/2014 |
| EP | 2772207 A2 | 9/2014 |
| EP | 2772208 A1 | 9/2014 |
| EP | 2772210 A2 | 9/2014 |
| EP | 2772211 A2 | 9/2014 |
| EP | 2772214 A2 | 9/2014 |
| EP | 3108845 A1 | 12/2016 |
| EP | 3421195 A1 | 1/2019 |
| EP | 3449850 A1 | 3/2019 |
| JP | H08-11071 A | 1/1996 |
| JP | 2001-310277 A | 11/2001 |
| JP | 2005-131417 A | 5/2005 |
| JP | 2005-305585 A | 11/2005 |
| JP | 2006-326157 A | 12/2006 |
| JP | 2006-334695 A | 12/2006 |
| JP | 2007-111148 A | 5/2007 |
| JP | 2008-212349 A | 9/2008 |
| JP | 2009-11809 A | 1/2009 |
| JP | 2009-268592 A | 11/2009 |
| JP | 2012-040202 A | 3/2012 |
| JP | 2012-131014 A | 7/2012 |
| JP | 2012-148379 A | 8/2012 |
| JP | 5198014 B | 5/2013 |
| JP | 2014-500152 A | 1/2014 |
| JP | 2015-154895 A | 8/2015 |
| WO | 2008/070556 A1 | 6/2008 |
| WO | 2012-054829 A2 | 4/2012 |
| WO | 2016/018618 A1 | 2/2016 |
| WO | 2017/145340 A1 | 8/2017 |

OTHER PUBLICATIONS

Partial Translation of International Search Opinion, Application No. PCT/JP2016/065955, dated Aug. 16, 2016.
Translation of International Search Report, Application No. PCT/JP2016/055717, dated Apr. 26, 2016.
Translation of International Search Report, Application No. PCT/JP2016/055710, dated Apr. 26, 2016.
Non-Final Office Action for U.S. Appl. No. 16/110,586, dated Jan. 27, 2021.

* cited by examiner

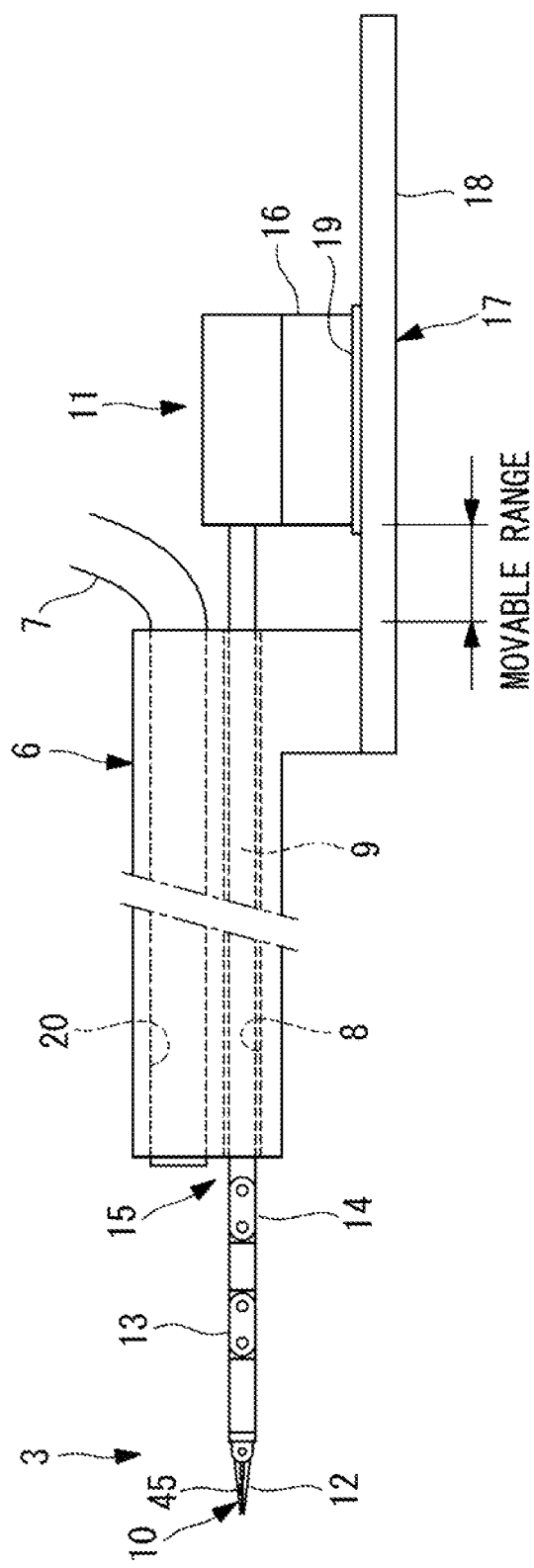

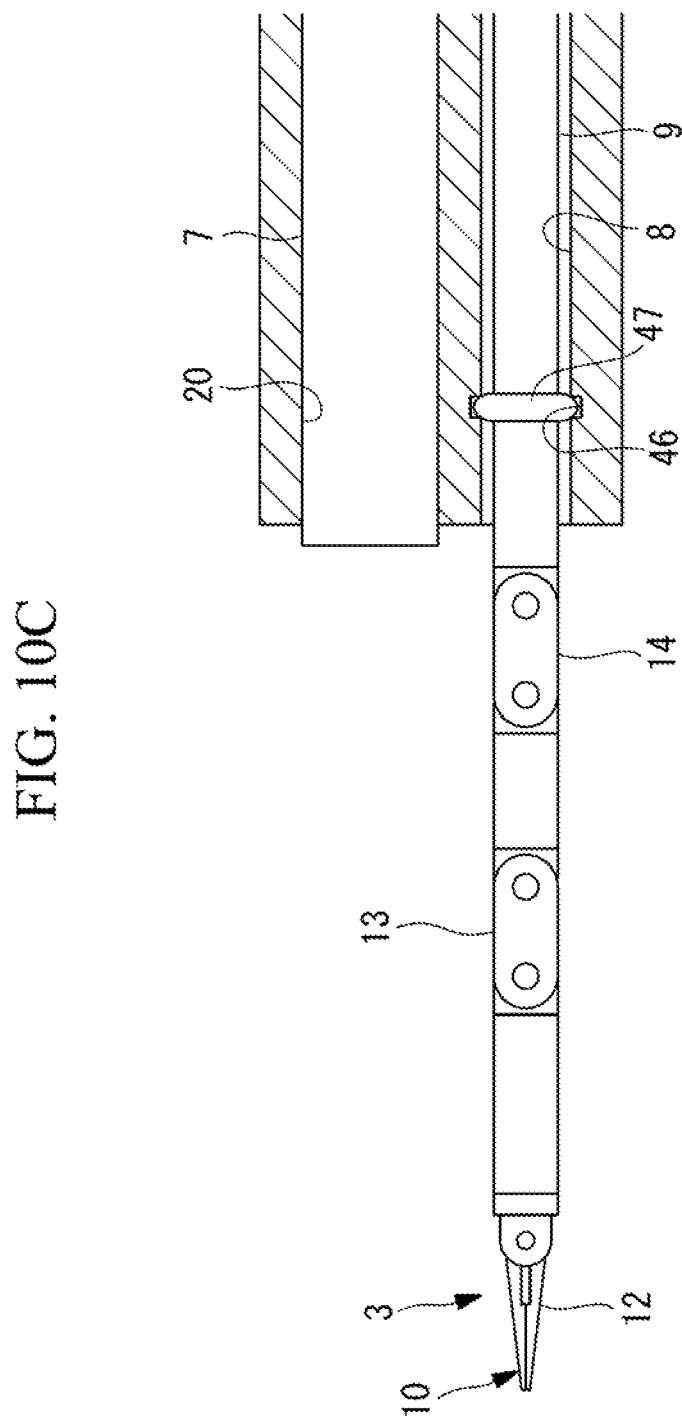

Set Position of projection

Adjust rolling axis and
push the "OK" button
after confirmation of
all joints on screen.

MANIPULATOR SYSTEM AND OPERATING METHOD THEREOF

CROSS-REFERENCE TO RELATED APPLICATIONS

This is a continuation of International Application PCT/JP2016/055717 which is hereby incorporated by reference herein in its entirety.

FIELD

The present invention relates to a manipulator system and an operating method thereof.

BACKGROUND

There is a known manipulator system that includes a multi-joint treatment tool and that employs a master-slave system (for example, see Japanese Unexamined Patent Application, Publication No. 2008-212349). In this manipulator system, the position of a manipulator that is made to protrude from a distal end of a forceps channel provided in an inserted portion is detected, and joint angles of a portion of the manipulator located inside the forceps channel are set so as to be along the shape of the forceps channel.

The teachings of Japanese Unexamined Patent Application, Publication No. 2008-212349 are incorporated by reference in its entirety herein for all purposes.

SUMMARY

An aspect of the present invention is a manipulator system including: a manipulator that is provided with an elongated flexible portion, a movable portion provided at a distal end of the flexible portion, and a driving portion that is provided at a proximal end of the flexible portion and that drives the movable portion; an inserted portion that includes a channel through which the manipulator is made to pass and that possesses flexibility; a reciprocating portion that moves the driving portion forward and backward in a longitudinal direction of the flexible portion, thus causing the movable portion to be protruded from and retracted into a distal end of the channel; a movable-portion-state identifying portion that identifies a state of the movable portion; a restricting portion that, when the movable-portion-state identifying portion identifies the movable portion to be in a protruded state in which the entire movable portion is made to protrude from the distal end of the channel, restricts the driving portion from being moved backward any farther by the reciprocating portion; and a restriction releasing portion that, when the movable-portion-state identifying portion identifies the movable portion to be in a retractable state in which retraction thereof into the channel is possible, releases the restriction by the restricting portion.

In addition, another aspect of the present invention is a manipulator-system operating method including: a movable-portion-state identifying step of, in a state in which a manipulator provided with a movable portion at a distal end of an elongated flexible portion and a driving portion that drives the movable portion at a proximal end is inserted into a channel of an inserted portion that possesses flexibility and a bent shape thereof is set, identifying a state of the movable portion; a restricting step of, when the movable portion is identified to be in a protruded state in which the entire movable portion is made to protrude from a distal end of the channel in the movable-portion-state identifying step, restricting the driving portion from being moved backward from that position; and a restriction releasing step of, in the state in which the backward movement is restricted in the restricting step, releasing the restriction when the movable portion is identified to be in a retractable state in which retraction thereof into the channel is possible in the movable-portion-state identifying step.

BRIEF DESCRIPTION OF THE DRAWINGS

FIG. 5A is a side view showing a state in which the entire movable portion of the manipulator of the manipulator system in FIG. 1 is made to protrude from a distal end of an overtube.

FIG. 10C is a partial longitudinal cross-sectional view showing a state in which the movable portion is recognized, by the state recognizing portion in FIG. 10B, to be in a protruded state in which the entire movable portion is made to protrude from the distal end of the overtube.

DETAILED DESCRIPTION

A manipulator system 1 and an operating method thereof according to an embodiment of the present invention will be described below with reference to the drawings.

Figure 1:
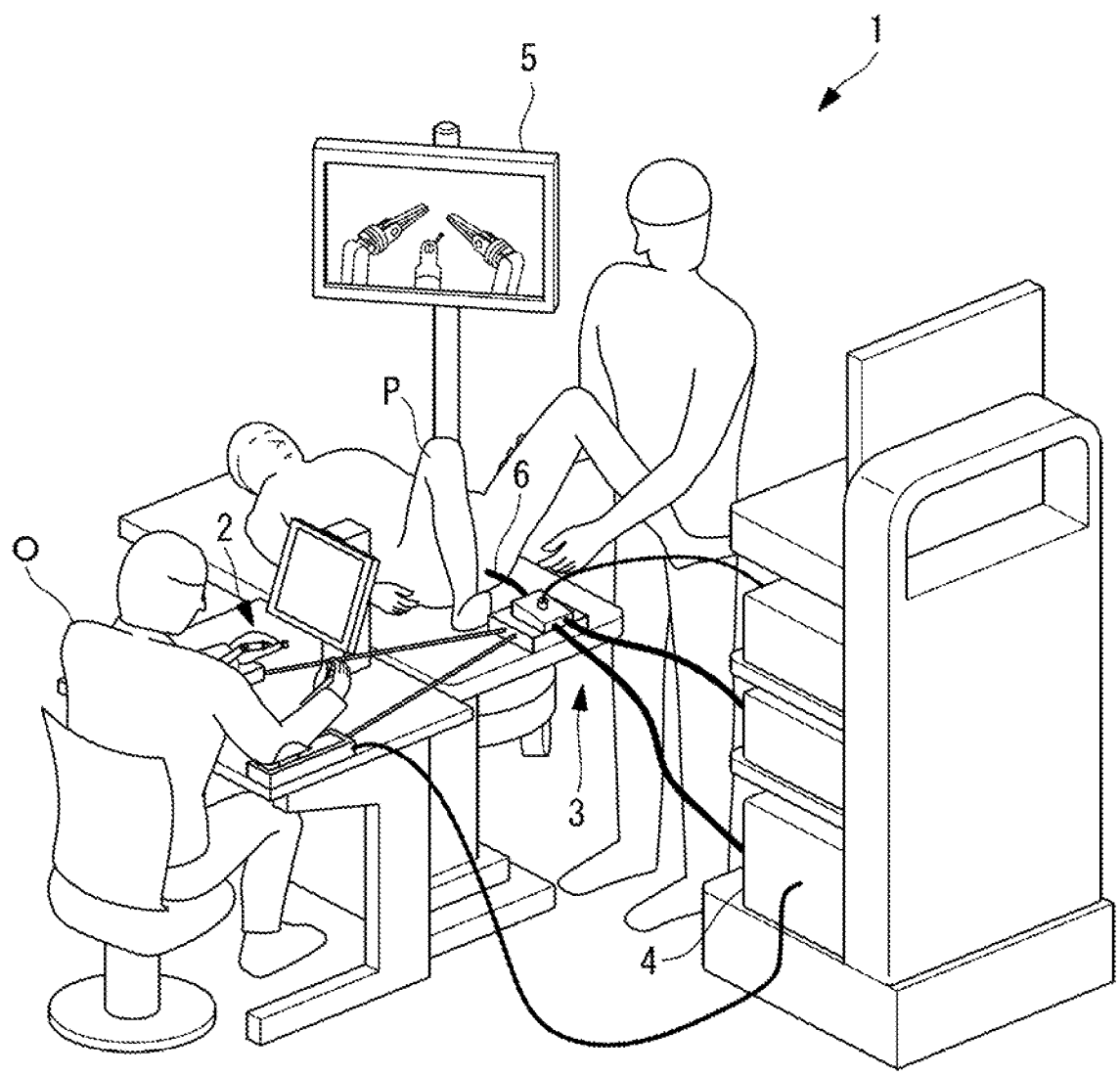
FIG. 1 is an overall configuration diagram showing a manipulator system according to an embodiment of the present invention.
Figure 2:
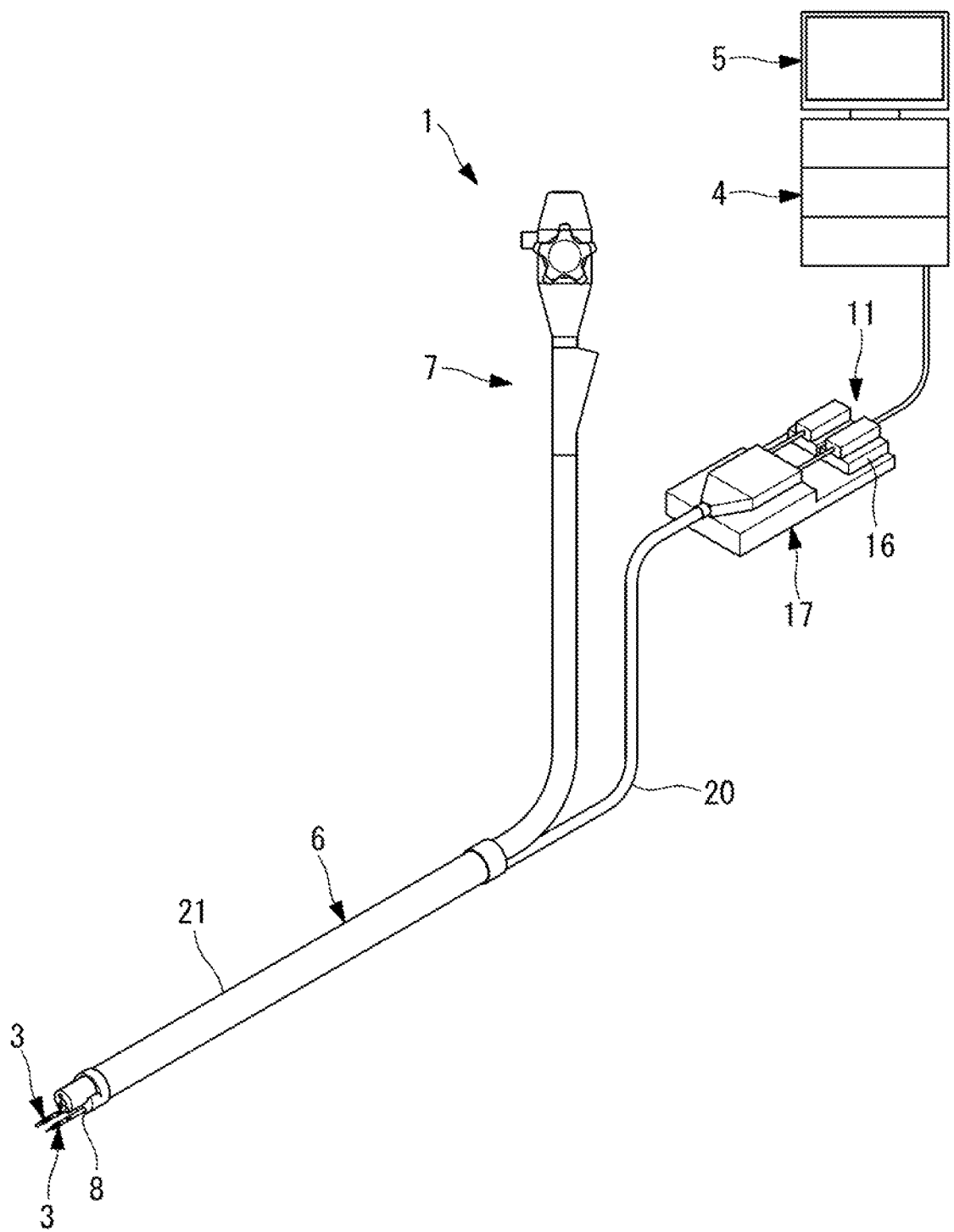
FIG. 2 is a perspective view showing a portion of the manipulator system in FIG. 1.

As shown in FIGS. 1 and 2, the manipulator system 1 according to this embodiment is provided with: a manipulation input portion 2 that is manipulated by an operator O; an overtube (inserted portion) 6 that is inserted into a body cavity of a patient P; a manipulator 3 and an endoscope (image-acquisition portion) 7 that are individually inserted into channels 8 of the overtube 6; a control portion 4 that controls the manipulator 3 on the basis of manipulation of the manipulation input portion 2; and a monitor (display portion) 5. In the example shown in FIG. 2, two manipulators 3 are provided and are individually inserted into the two channels 8 of the overtube 6; however, in the following, only one of the manipulators 3 will be described.

Figure 3:
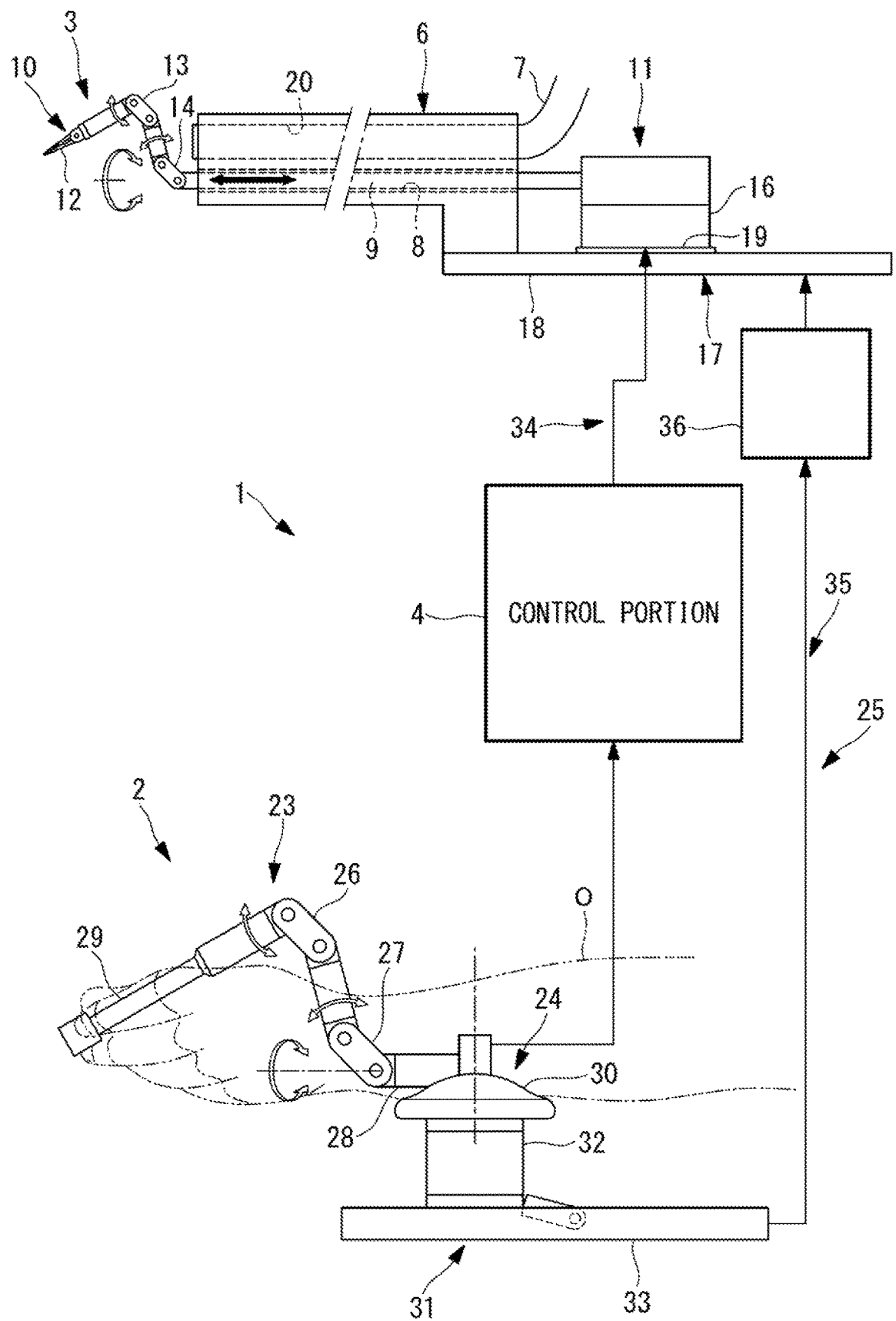
FIG. 3 is a diagram showing a manipulator, a manipulation input portion, and a control portion employed in the manipulator system in FIG. 1.

As shown in FIG. 3, the manipulator 3 is provided with: an elongated flexible portion 9 that is inserted into the body interior of the patient P via the channel 8 of the overtube 86; a movable portion 10 that is provided at a distal end of the flexible portion 9; and a driving portion 11 that is disposed on a proximal-end side of the inserted portion 6, and that drives the movable portion 10 by means of a motive-power transmitting member (not shown) such as a wire or the like.

The movable portion 10 is provided with: a treating portion 12 that is disposed at the most distal end thereof and that acts on an affected portion in the body to perform treatment thereof; and a plurality of joints 13, 14, and 15 that change the distal-end position and the attitude of the treating portion 12. The treating portion 12 is, for example, a gripping forceps, a high-frequency knife, or the like.

In addition, as shown in FIG. 3, the manipulator 3 is connected to the driving portion 11 in an attachable/detachable manner and is provided with: a motor unit 16 that has, built therein, an electrical driving source (not shown) such as a motor or the like that imparts a motive power to the driving portion 11; and a reciprocating mechanism (reciprocating portion) 17 that linearly moves the motor unit 16.

The reciprocating mechanism 17 is provided with: a base 18; and a slider 19 that supports the motor unit 16 so as to allow linear movement thereof with respect to the base 18.

The overtube 6 is a tube formed of a material possessing flexibility and is provided, as shown in FIGS. 2 and 3, with: a distal-end-side tubular portion 21 including the manipulator channel (channel) 8 through which the manipulator 3 is made to pass and an endoscope channel 20 through which the endoscope 7 is made to pass; and a proximal-end-side tubular portion 22 that extends toward a proximal end of the manipulator channel 8 from a proximal end of the distal-end-side tubular portion 21.

As shown in FIG. 3, the manipulation input portion 2 is provided with: a first manipulation portion 23 that is gripped and manipulated by the hand of the operator O; a second manipulation portion 24 that is manipulated by the wrist or arm of the operator O; and an instruction transmitting portion 25 that transmits manipulation instructions input via these manipulation portions 23 and 24 to the manipulator 3.

The first manipulation portion 23 is configured to have a similar shape to that of the movable portion 10 of the manipulator 3, and distal-end portion 29 that is supported by joints 26, 27, and 28, which are provided in the same number as those of the movable portion 10, is gripped by the hand of the operator O so as to be moved by his/her palm or fingers. The first manipulation portion 23 is provided with sensors (not shown) that detect the angles of the individual joints 26, 27, and 28 constituting the first manipulation portion 23. Note that the first manipulation portion 23 is not limited to that having shape similar to that of the movable portion 10, and the first manipulation portion 23 may have a non-similar shape.

The sensors are configured so as to generate electrical signals in accordance with the angles of the individual joints 26, 27, and 28. By doing so, each of the first manipulation portions 23 is configured so that the manipulation instructions are input by means of the palm or the fingers of the operator O, thus making it possible to generate motion instructions in the form of electrical signals.

In addition, the distal-end portion 29 of the first manipulation portion 23 is provided with an input portion (not shown) with which the operator O inputs confirmation about the fact that the entire movable portion 10 has been made to protrude from the distal end of the manipulator channel 8, as described later.

The second manipulation portion 24 is provided with: an arm-resting base 30 that is secured to base portion of the first manipulation portion 23; and a linear motion mechanism 31 that supports the arm-resting base 30 and the first manipulation portion 23 in an integrally movable manner. The arm-resting base 30 is disposed at a position at which, when the operator O grips the distal-end portion 29 of the first manipulation portion 23, a portion of his/her arm near the wrist of the hand gripping the distal-end portion 29 is appropriately placed thereon.

Figure 4:
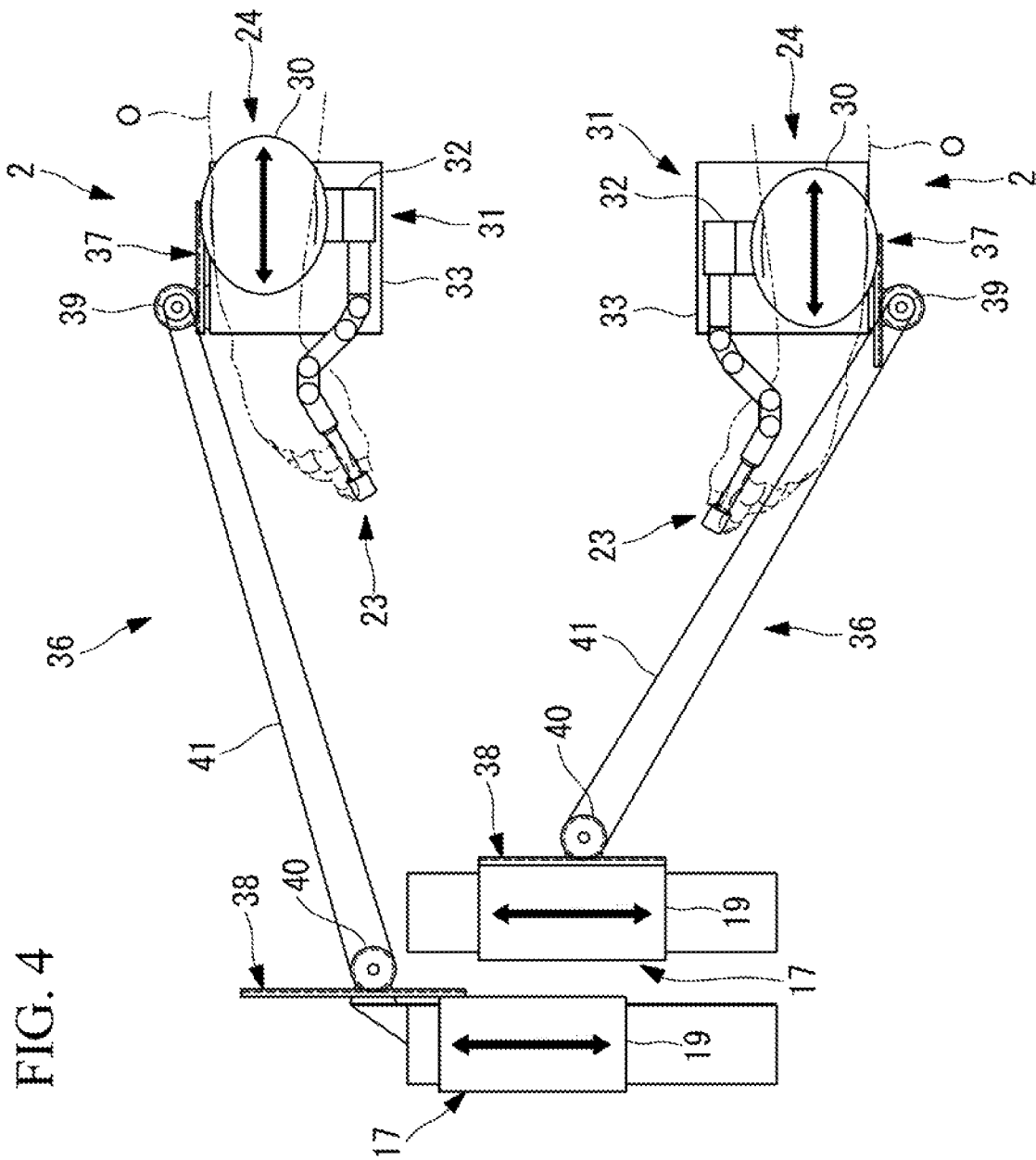
FIG. 4 is a plan view for explaining a second manipulation portion, an instruction transmitting portion, and a reciprocating mechanism of the manipulation input portion of the manipulator system in FIG. 1.

The linear motion mechanism 31 is provided with: a slider 32 that secures the arm-resting base 30 and the first manipulation portion 23; and a linear guide 33 that supports the slider 32 so as to be movable in a horizontal direction, as indicated by the filled arrows in FIGS. 3 and 4. By moving the slider 32 in the horizontal direction by means of the arm placed on the arm-resting base 30, it is possible to move the position of the first manipulation portion 23 while maintaining the attitude in which the first manipulation portion 23 is gripped. By doing so, the second manipulation portion 24 is configured so that the manipulation instructions are input by means of the wrist or the arm of the operator O, thus making it possible to generate the motion instructions in the form of mechanical driving forces of the two sliders 32 by using the forces applied via the inputs made by means of the wrists or the arms. Note that, in addition to the case in which the slider 32 generates the motion instructions in the form of the mechanical driving forces, a system in which the motion instructions are generated in the form of electrical driving forces may be employed.

The instruction transmitting portion 25 is provided with an electrical-signal transmitting portion 34 that connects the first manipulation portion 23 and the driving portion 11; and a mechanical-motive-power transmitting portion 35 that connects the second manipulation portion 24 and the reciprocating mechanism 17.

The electrical-signal transmitting portion 34 transmits the motion instructions in the form of electrical signals generated by the first manipulation portion 23 to the control portion 4, and supplies the instruction signals generated by the control portion 4 to the individual motors of the motor unit 16. The control portion 4 calculates rotational movement amounts and rotational speeds of the individual motors of the motor unit 16 on the basis of the motion instructions generated by the first manipulation portion 23, thus controlling the individual motors.

As shown in FIG. 3, the mechanical-motive-power transmitting portion 35 is provided with a transmitting portion 36 that converts linear motions in which each of the sliders 32 of the manipulation input portion 2 is moved back and forth to linear motions of the reciprocating mechanism 17.

As shown in FIG. 4, the transmitting portion 36 is provided with: a first rack-and-pinion mechanism 37 that converts linear movement amounts of the slider 32 of the manipulation input portion 2 to rotational angles; a second rack-and-pinion mechanism 38 that converts rotational motions to linear movement amounts of a slider 19 of the reciprocating mechanism 17; pulleys 39 and 40 that are separately secured to pinion gears of the rack-and-pinion mechanisms 37 and 38; and a belt 41 that are wound around the pulleys 39 and 40.

In this embodiment, the motion range of the slider 32 of the linear motion mechanism 31 corresponds to the motion range of the slider 19 of the reciprocating mechanism 17 that moves the manipulator 3 in longitudinal direction of the flexible portion 9 with respect to the overtube 6. In other words, when the slider 32 is moved between the most front-end position and the most rear-end position, it is possible to move the manipulator 3 between a treating state in which the entire movable portion 10 provided at the distal end of the manipulator 3 is made to protrude forward from the manipulator channel 8 of the overtube 6, as shown in FIG. 5A, and an accommodated state in which the entire movable portion 10 is accommodated in the manipulator channel 8 of the overtube 6, as shown in FIG. 6.

Also, in this embodiment, at an intermediate position in the motion range of the slider 19 of the reciprocating mechanism 17, a restricting portion 42 that restricts further backward movement of the slider 19 is provided in such a way that the position thereof can be adjusted.

Figure 7:
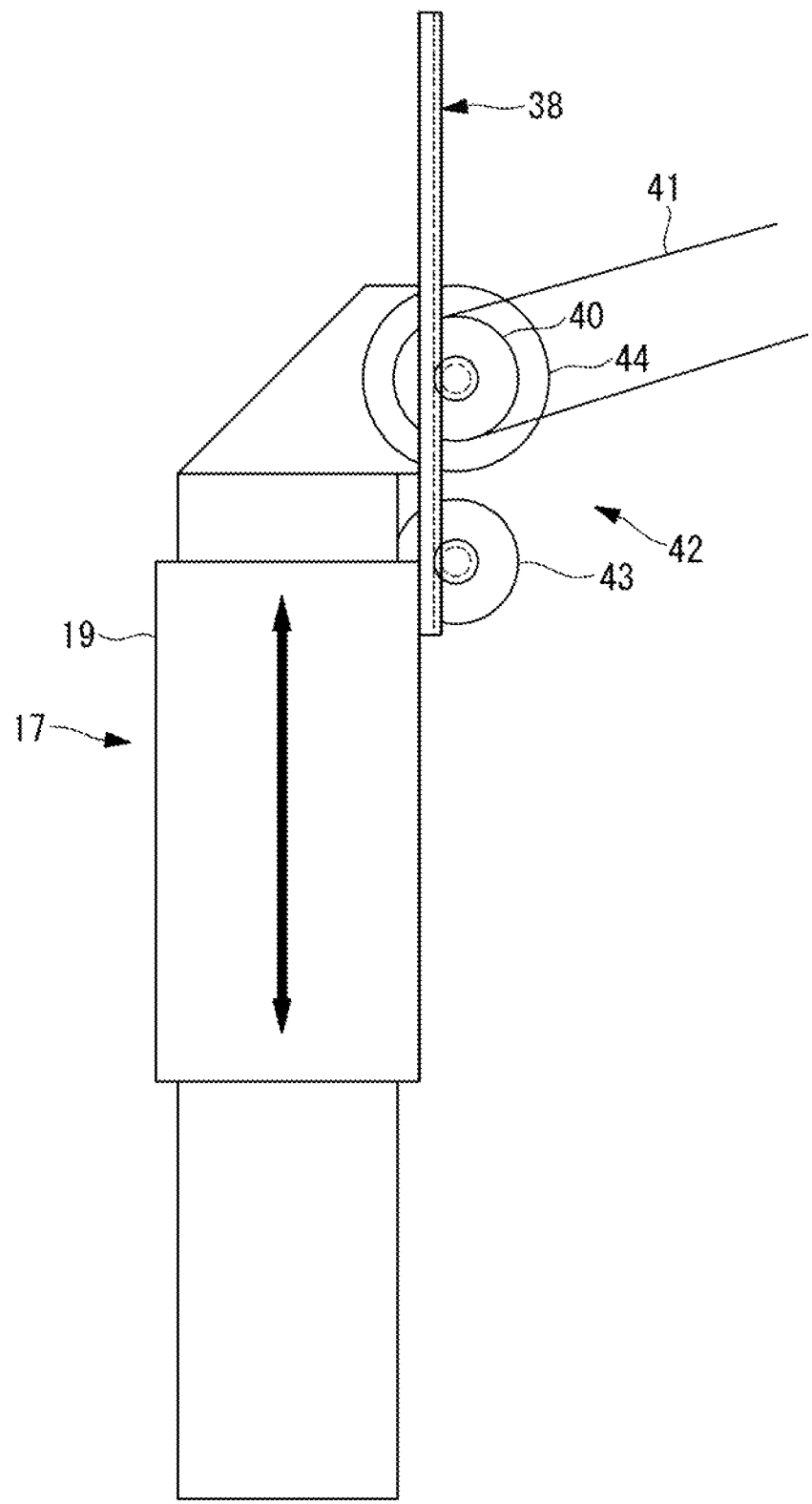
FIG. 7 is a diagram showing an example of a restricting portion of the manipulator system in FIG. 1.

For example, as shown in FIG. 7, the restricting portion 42 is provided with: an encoder 43 that detects the reciprocating position of the rack gear of the second rack-and-pinion mechanism 38; and a brake 44 that restricts the rotation of the pinion gear when the encoder 43 detects a predetermined position.

Figure 5B:
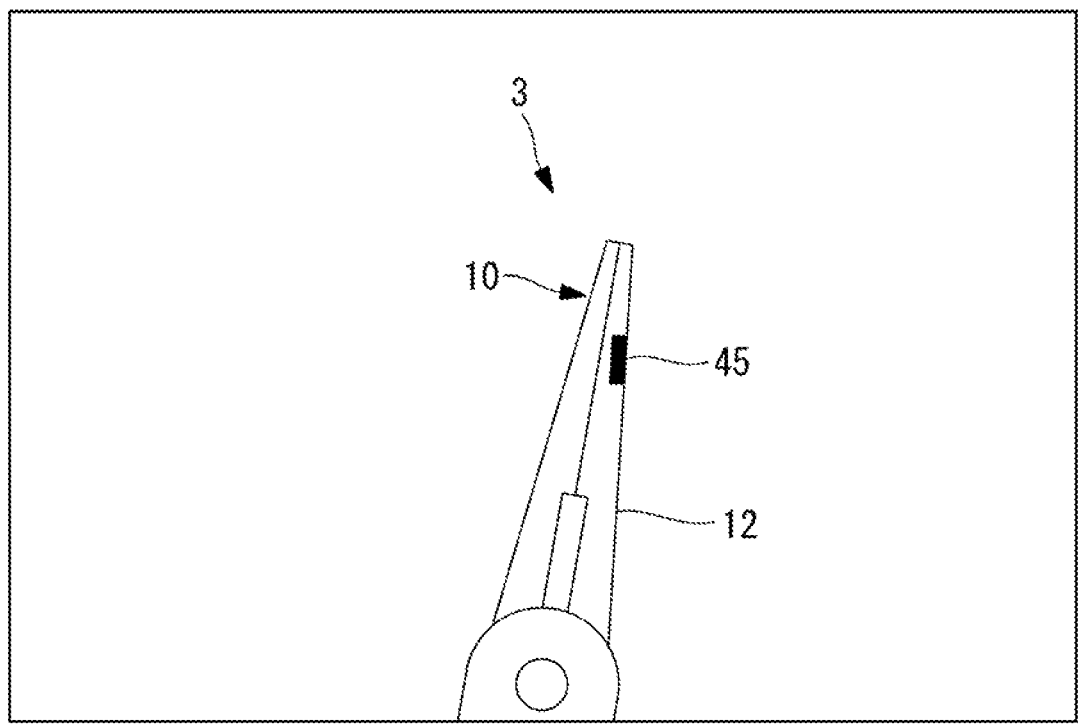
FIG. 5B is a diagram showing an example of an endoscope image, in which a marker is displayed, acquired by using an endoscope passing through the overtube of the manipulator system in FIG. 1.
Figure 6:
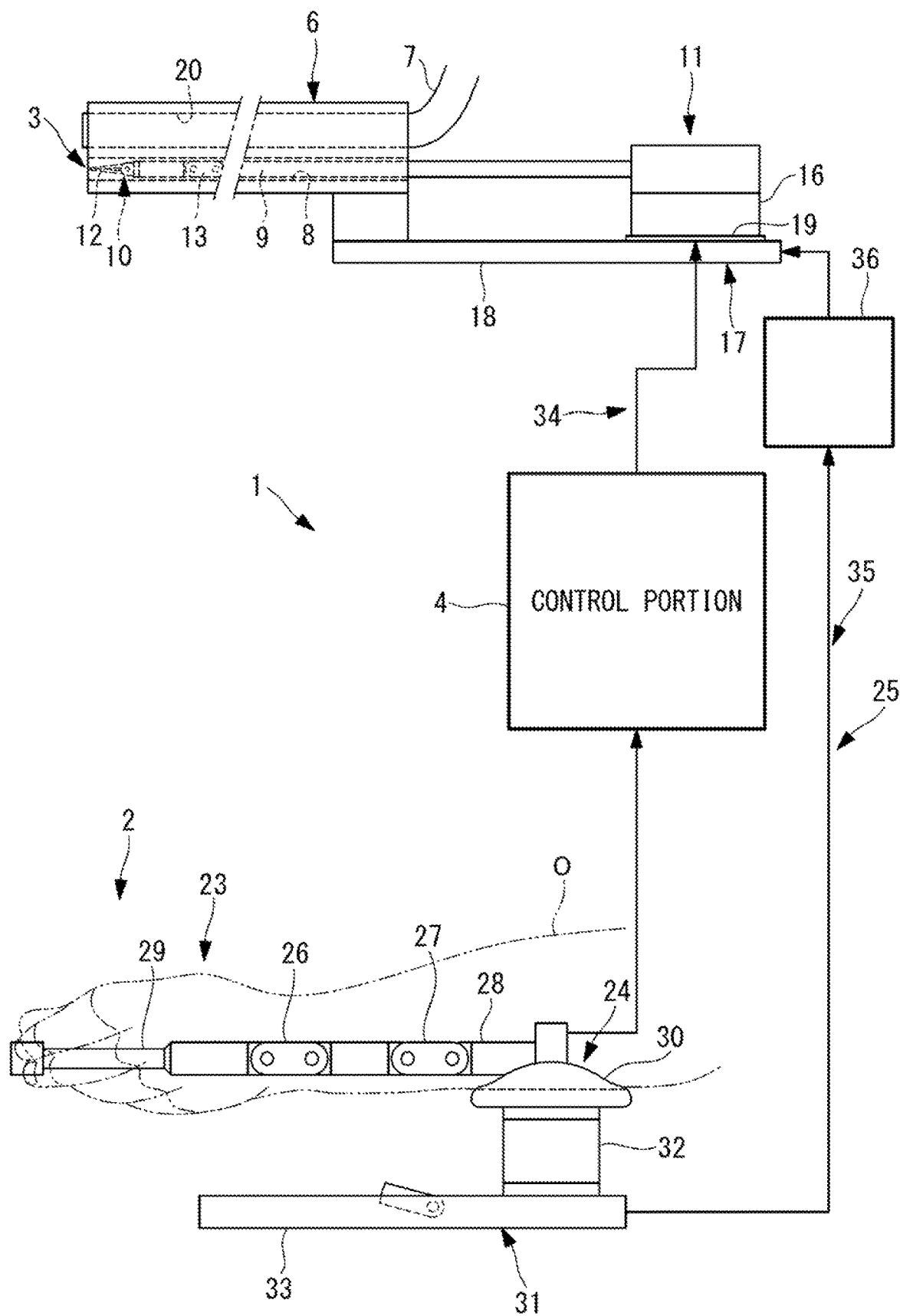
FIG. 6 is a diagram showing an accommodated state in which the entire movable portion of the manipulator system in FIG. 1 is accommodated in a manipulator channel of the overtube.

In addition, in this embodiment, as shown in FIGS. 5A and 5B, a marker 45 is provided on the distal-end side of the treating portion 12. The marker 45 may be formed of paint, a rubber cover, printed letters, or a feature shape of the movable portion 10 (a specific joint, logo, or the like).

Furthermore, in this embodiment, when the operator O confirms the marker 45 of the treating portion 12 in an endoscope image displayed on the monitor 5 and when the operator O inputs the confirmation via the input portion (not shown) provided in the first manipulation portion 23 of the manipulation input portion 2, the control portion (movable-portion-state identifying portion) 4 initializes the rotational angles of the encoder 43 and the treating portion 12, and causes the slider 19 to be moved forward by a pre-set distance from the position at which the marker 45 is displayed on the monitor 5 to a position at which a state in which the entire movable portions 10 is made to protrude on the distal-end side of the channel 8 is achieved. Subsequently, at the moment when the slider 19 is placed at the position reached after being moved by the pre-set distance, the control portion 4 operates the brake 44, thus restricting the backward movement of the rack gear (restricted mode).

Furthermore, as shown in FIG. 6, when the operator O manipulates the first manipulation portion 23 so that all of the joints constituting the first manipulation portion 23 take shapes that allow accommodation thereof (for example, a shape extending in a straight line), and thus, when the movable portion 10 of the manipulator 3 take a shape that is along the longitudinal direction of the flexible portion 9, the control portion (movable-portion-state identifying portion, restriction releasing portion) 4 releases the restriction applied by the brake 44 (retractable mode).

An operating method of the thus-configured manipulator system 1 according to this embodiment will be described below.

Figure 8A:
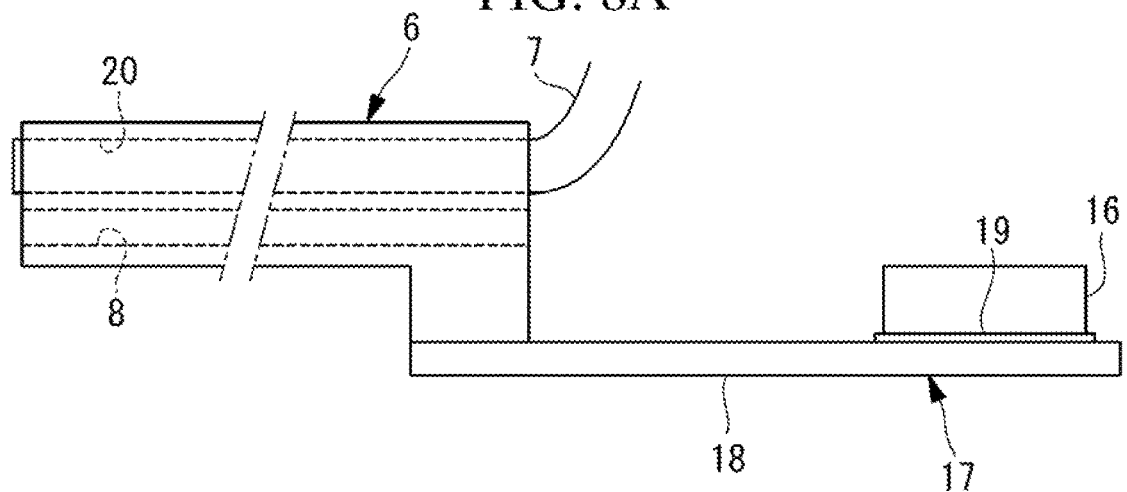
FIG. 8A is a diagram showing a state in which the endoscope is inserted into an endoscope channel of the overtube of the manipulator system in FIG. 1.

In order to treat an affected portion in the body of the patient P by using the manipulator system 1 according to this embodiment, as shown in FIG. 8A, the endoscope 7 and the overtube 6 are inserted into the body cavity of the patient P in the state in which the endoscope 7 is inserted into the endoscope channel 20 of the overtube 6, and an image acquired by using the endoscope 7 is displayed on the monitor 5.

Figure 9:
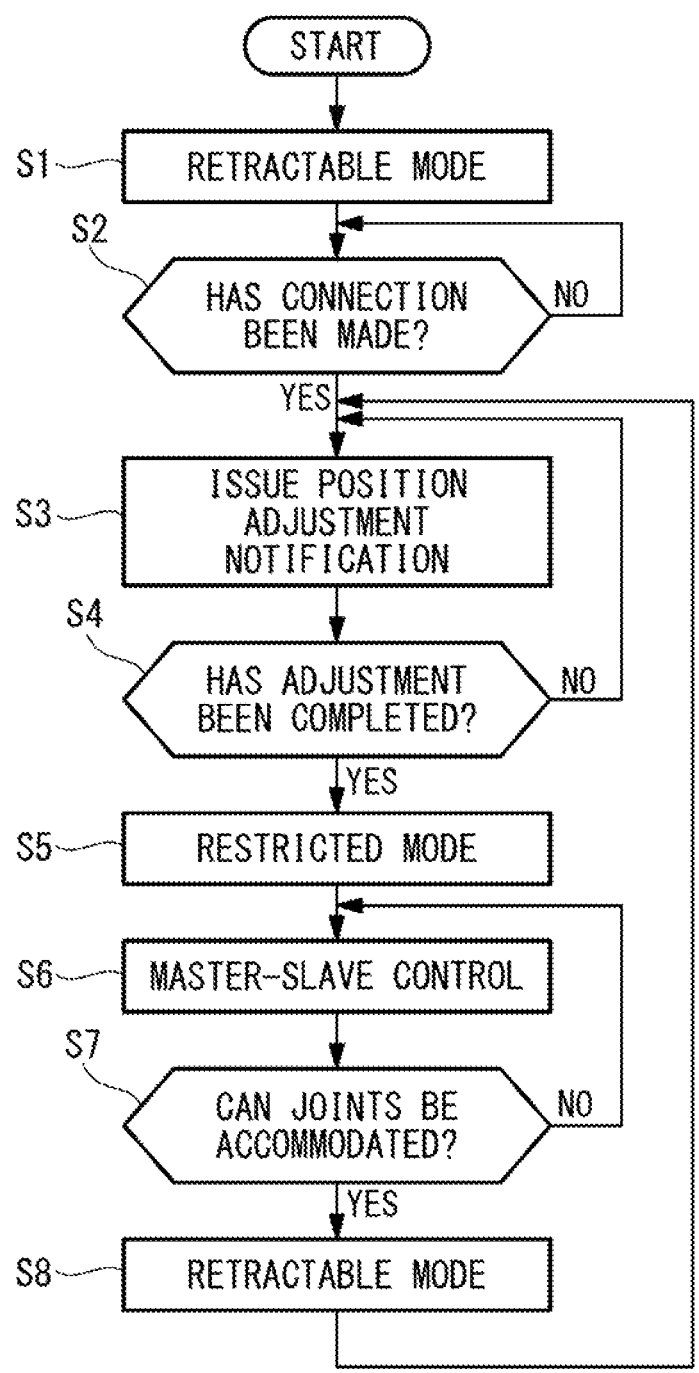
FIG. 9 is a flowchart for explaining an operating method of the manipulator system in FIG. 1.

As shown in FIG. 9, the restriction by the restricting portion 42 is released by the control portion 4, thus entering the retractable mode (step S1).

Figure 8B:
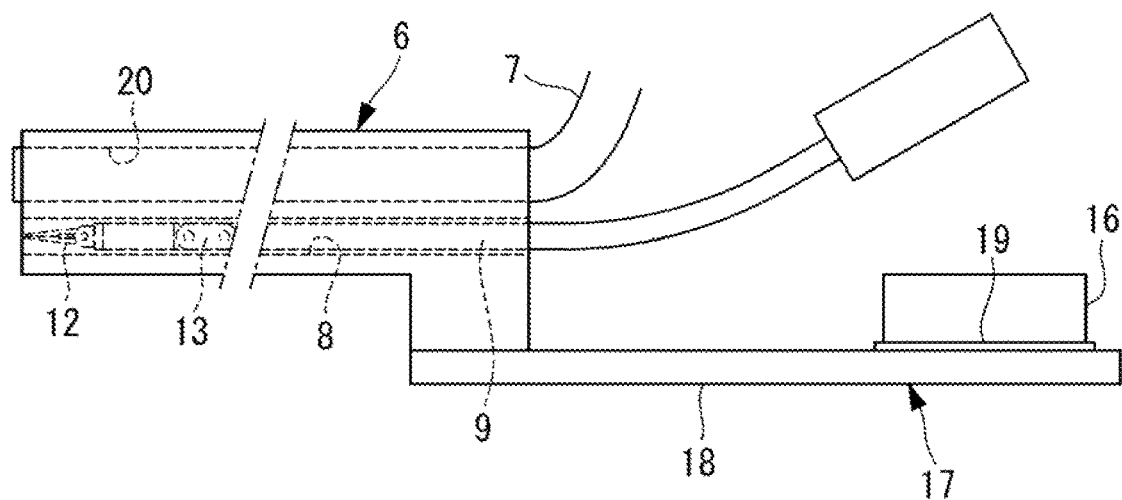
FIG. 8B is a diagram showing a state in which the manipulator is inserted into the manipulator channel of the overtube of the manipulator system in FIG. 1.

Then, as shown in FIG. 8B, the slider 19 of the reciprocating mechanism 17 is placed at the position at which the slider 19 is moved backward the farthest, thus being restricted by the brake 44, and the movable portion 10 and the flexible portion 9 of the manipulator 3 is inserted into the body of the patient P via the manipulator channel 8.

In addition, in the case in which the slider 19 is not at the position at which the slider 19 is moved backward the farthest, the operator O is notified, by means of the monitor 5 or a sound, so as to move the slider 19 to that position. At this time, only in the case in which the slider 19 is at the position at which the slider 19 is moved backward the farthest, detection is made by a detection portion (not shown), such as a sensor or the like, that outputs signals and that is provided in the reciprocating mechanism 17, thus determining the position thereof.

Figure 8C:
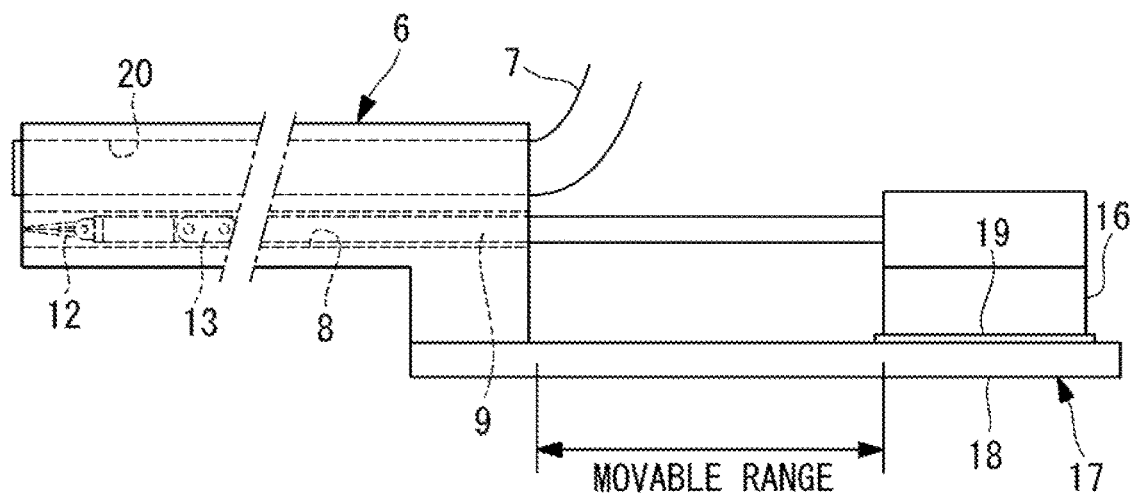
FIG. 8C is a diagram showing a state in which a driving portion of the manipulator in FIG. 8B is connected to a motor unit.

Then, in the case in which the detection portion detects that the slider 19 is placed at the position at which the slider 19 is moved backward the farthest, as shown in FIG. 8C, the system stands by until the driving portion 11 of the manipulator 3 is connected to the motor unit 16 secured to the slider 19 of the reciprocating mechanism 17 (step S2). Because the slider 19 is placed at the position at which the sliders 19 is moved backward the farthest at the moment when the driving portion 11 is connected to the motor unit 16, the entire movable portion 10 of the manipulator 3 is completely accommodated in the manipulator channel 8, as shown in FIG. 8C.

Next, the control portion 4 notifies the operator O, on the monitor 5, so as to adjust the reciprocating position of the manipulator 3 by means of the slider 19 of the reciprocating mechanism 17, and releases the restriction by the brake 44.

In response, the operator O applies a force in directions in which the slider 32 secured to the arm-resting base 30 of the second manipulation portion 24 is moved forward. The slider 32 is moved n the direction in which the force is applied, and the linear movement amount thereof is converted to a rotational angle by the first rack-and-pinion mechanism 37.

The linear movement amount that has been converted to the rotational angle of the first rack-and-pinion mechanism 37 is transmitted to the second rack-and-pinion mechanism 38 via the pulley 39 and the belt 41 and is converted to a linear movement amount of the slider 19 of the reciprocating mechanism 17. Because the motor unit 16 is secured to the slider 19 of the reciprocating mechanism 17, the driving portion 11, the flexible portion 9, and the movable portion 10 connected to the motor unit 16 are integrally moved along the longitudinal direction of the flexible portion 9. By doing so, the treating portion 12 positioned at the distal end of the movable portion 10 is manually moved forward.

When the operator O continues to move the manipulator 3, the movable portion 10 provided at the distal end of the manipulator 3 is made to protrude from the distal end of the manipulator channel 8 of the overtube 6. The operator O continues to move the slider 32 of the second manipulation portion 24 forward while checking the image acquired by using the endoscope 7 on the monitor 5.

Then, when the treating portion 12 is made to protrude from the distal end of the manipulator channel 8, as shown in FIG. 5A, the marker 45 provided on the manipulator 3 is displayed on the monitor 5, as shown in FIG. 5B. By doing so, the operator O can recognize the fact that the treating portion 12 have been made to protrude from the distal end of the manipulator channel 8 (movable-portion-state identifying step S3).

Also, subsequently, whether or not position adjustment has been completed is determined (step S4). In the case in which it is determined that the adjustment has not been completed, the operator O is notified on the monitor 5 to execute the position adjustment again. In the case in which the operator O makes an input indicating the fact that he/she has recognized the marker 45 via the input portion of the first manipulation portion 23, and thus, it is determined that the position adjustment has been completed, the encoder 43 is initialized. Note that, because the movable portion 10 is positioned inside the overtube 6 at this moment, it is not possible to operate the movable portion 10.

When the operator O makes an input indicating that he/she has recognized the marker 45, the control portion 4 moves the slider 19 forward by the preset-distance from the position at which the marker 45 is displayed on the monitor 5 to the position at which the state in which the entire movable portion 10 is made to protrude on the distal-end side from the channel 8 is achieved (the operator O may move the slider 19 forward). When the fact that the slider 19 has been placed at the position at which the slider 19 is moved forward by the pre-set distance is detected, the restricted mode is achieved, in which the movement in the direction in which the manipulator 3 is moved backward farther than that initial position is restricted by the brake 44 (restricting step S5). Note that, at this moment, the control portion 4 initiates master-slave control that causes the manipulation input portion 2 and the manipulator 3 to work together (step S6).

In addition, regarding the initiation of the master-slave control, the manipulator system 1 may automatically initiate the master-slave control by detecting the fact that the slider 19 has been placed at the position at which the slider 19 has been moved forward. Alternatively, the manipulator system 1 may stand by until the operator O makes a manipulation (for example, pressing a switch in the manipulation input portion 2, pressing a button on a screen, or the like), and may automatically initiate the master-slave control by detecting this manipulation.

In order to manipulate the manipulation input portions 2 in this state, as shown in FIG. 4, the operator O grips the distal-end portions 29 of the first manipulation portions 23 with both hands, and places his/her arms on the arm-resting bases 30 of the second manipulation portions 24.

When the operator O moves, by means of the force applied by the palms or the fingers, the distal-end portions 29 of the first manipulation portions 23 being gripped by the operator O, the movement amounts thereof are detected by the sensors provided in the individual joints 26, 27, and 28, and are transmitted to the control portion 4 in the form of the electrical signals. The control portion 4 calculates the electrical motion instructions with which the individual joints 13, 14, and 15 of the movable portions 10 are moved so as to match the angles of the joints 26, 27, and 28 detected by the sensors, and supplies the motors of the motor units 16 connected to the individual joints 13, 14, and 15 with the electrical motion instructions. By doing so, the distal-end positions of the treating portions 12 provided at the distal ends of the movable portions 10 are electrically and precisely moved in accordance with the instructions given by means of the palms or the fingers.

With the manipulator system 1 according to this embodiment, when the slider 32 of the second manipulator portion 24 is moved forward, thus driving the movable portion 10 into the treating state, in which the movable portion 10 is made to protrude from the manipulator channel 8, from the accommodated state, in which the movable portion 10 is accommodated inside the manipulator channel 8 of the overtube 6, the brake 44 is not operating, and thus, the operator O can move the arm-resting base 30 back and forth without restriction on the movements thereof.

On the other hand, after the fact that the entire movable portion 10 has been made to protrude from the manipulator channel 8 is recognized by means of the endoscope image displayed on the monitor 5 and this information has been input via the input portion, the rotational angles of the encoder 43 and the treating portions 12 are initialized, and, when the encoder 43 is set at the initial position, the brake 44 is operated, thus making it impossible to move the arm-resting base 30 back any farther toward the proximal end thereof.

Once the movement of the arm-resting base 30 is restricted, because the operator O cannot move the slider 32 backward any farther, he/she can recognize that the movable portion 10 has been driven into the accommodated state from the protruded state. Therefore, it is possible to prevent the movable portion 10 from being retracted into the manipulator channel 8 by the operator O unintentionally excessively moving the arm-resting base 30 backward.

In other words, in the restricted mode, except for when the slider 32 of the arm-resting base 30 is moved backward to the initial position thereof, and thus, the further backward motion is restricted by means of the brake 44, it is possible to perform treatment by freely moving the movable portion 10 without limitation. Therefore, the movable portion 10 is prevented from being forcedly retracted into the manipulator channel 8 in the state in which the joints 13, 14, and 15 thereof are flexed, and thus, there is an advantage in that it is possible to prevent the distal end of the movable portion 10 from being moved in an unintended direction, and that it is possible to prevent an excessive load that would forcedly straighten the flexed joints 13, 14, and 15 of the movable portion 10 from acting on the joints 13, 14, and 15.

Then, the operator O, when he/she intentionally attempts to drive the movable portion 10 into the accommodated state, causes the individual joints 26, 27, and 28 constituting the first manipulation portion 23 to take the shapes that allow accommodation thereof, as shown in FIG. 6. For example, the joints are straightened (step S7). By doing so, because the individual joints 13, 14, and 15 constituting the movable portion 10 take the shapes that are along the longitudinal direction of the flexible portion 9, the control portion 4 stops the operation of the brake 44 (restriction releasing step S8, retractable mode). By doing so, the operator O can accommodate the movable portion 10 into the manipulator channel 8 by moving the slider 32 backward without forcing the movements thereof.

Figure 10A:
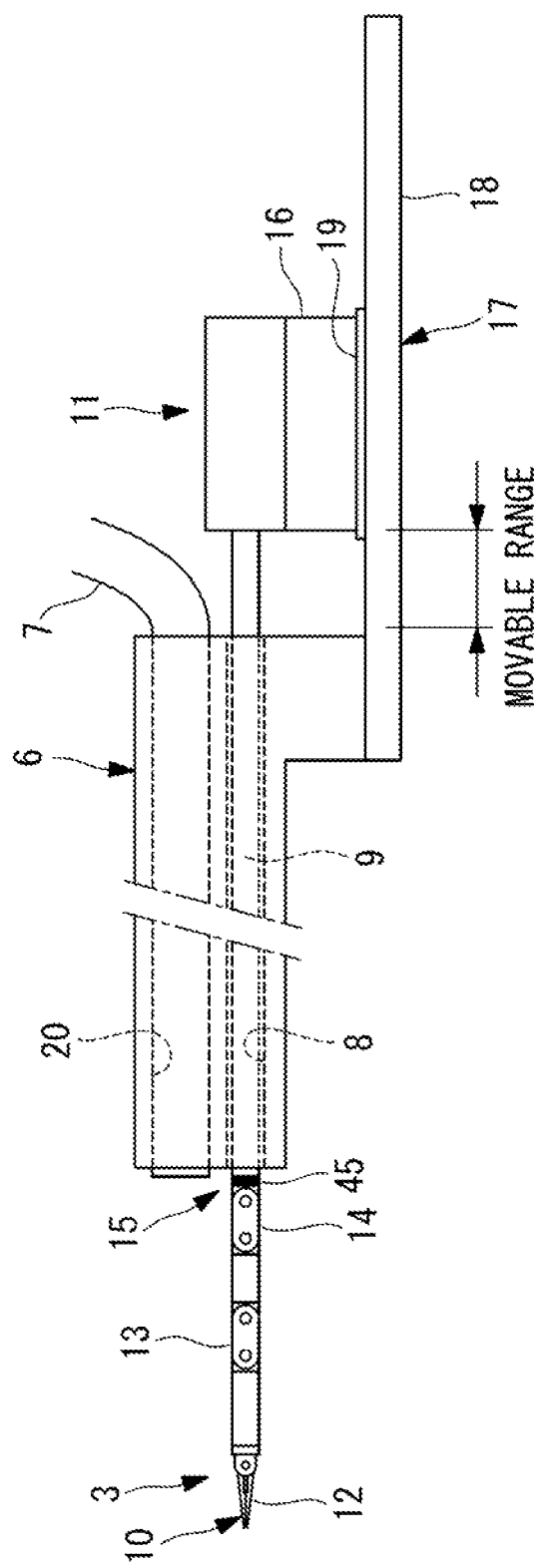
FIG. 10A is a partial longitudinal cross-sectional view showing a modification of a state recognizing portion of the manipulator system in FIG. 1.

Note that, although the manipulator system 1 according to this embodiment, in which the marker 45 is provided on the distal-end side of the treating portion 12, is employed, alternatively, as shown in FIG. 10A, it is permissible to employ a system in which, in a portion that is closer to the proximal end than the movable portion 10 is, the marker 45 is placed in the viewing field of the endoscope 7 in the state in which the entire movable portion 10 is made to protrude on the distal-end side of the channel 8.

By doing so, the operator O visually recognizes the fact that the entire movable portion 10 has been made to protrude from the distal end of the manipulator channel 8 by using the marker 45 in the endoscope image displayed on the monitor 5, and thus, the control portion 4 can initiate the master-slave control in which the manipulation input portion 2 and the manipulator 3 work together without requiring the operator O to manipulate the reciprocating mechanism 17.

In addition, regarding the initiation of the master-slave control, the manipulator system 1 may automatically initiate the master-slave control by detecting the fact that the slider 19 has been placed at the position at which the slider 19 has been moved forward. Alternatively, the manipulator system 1 may stand by until the operator O makes a manipulation (for example, pressing a switch in the manipulation input portion 2, pressing a button on a screen, or the like), and may automatically initiate the master-slave control by detecting this manipulation.

Figure 10B:
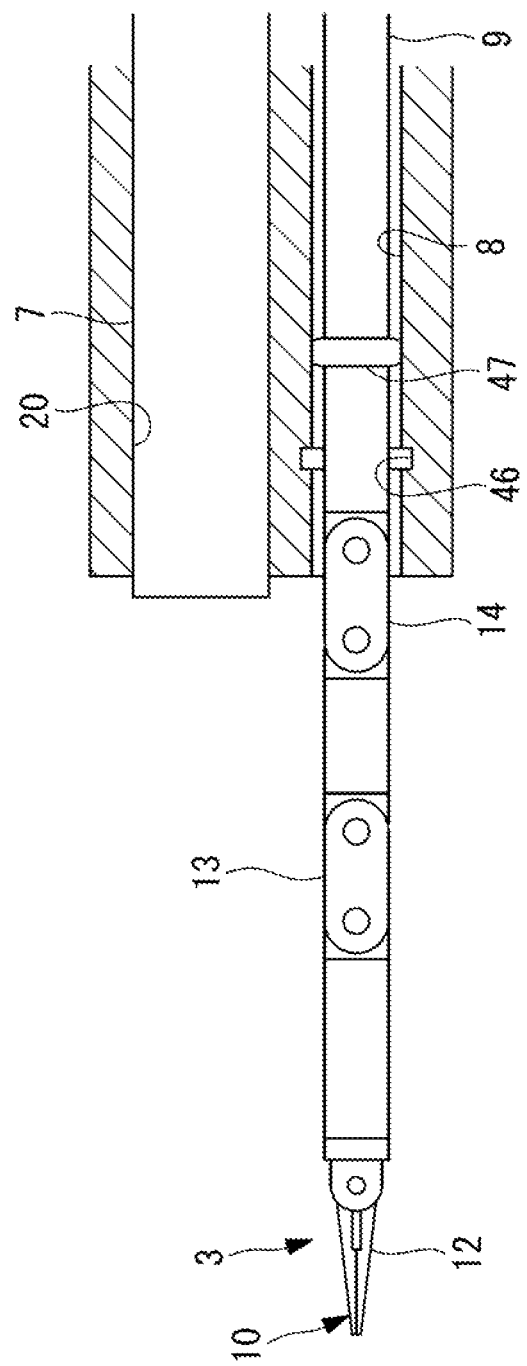
FIG. 10B is a partial longitudinal cross-sectional view showing a modification of the state recognizing portion of the manipulator system in FIG. 10A.

In addition, as shown in FIG. 10B, a depression 46 may be provided on an inner surface of the manipulator channel 8, and a protrusion (engaging portion) 47 that engage with the depression 46 at the moment when the entire movable portion 10 is made to protrude from the distal end of the manipulator channel 8 may be provided on an outer surface of the manipulator 3. The protrusion 47 is, for example, a ring that can be elastically deformed and that is made of rubber or the like.

As shown in FIG. 10C, when the protrusion 47 and the depression 46 are aligned with each other when the manipulator 3 is moved, the expanded shape of the protrusion 47 is restored and the protrusion 47 engages with the depression 46. By doing so, the operator O can recognize the fact that the entire movable portion 10 has been made to protrude from the distal end of the manipulator channel 8 by sensing a force (clicking sensation).

The protrusion 47 may be provided on the inner surface of the manipulator channel 8, and the depression (engaging portion) 46 that engages with the protrusion 47 may be provided on the outer surface of the manipulator 3.

In addition, instead of having the operator O input the information about the fact that the marker 45 has been recognized in the endoscope image via the input portion provided at the distal-end portion 29 of the manipulation input portion 2, the input may be made via manipulation of a button displayed on the monitor 5 in a GUI thereof.

Figure 11A:
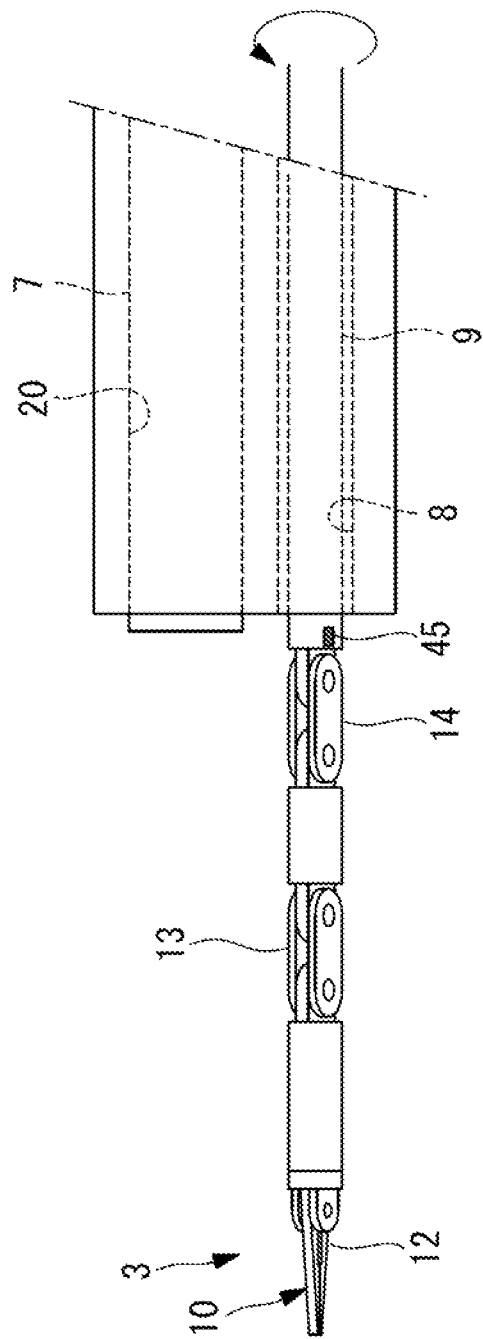
FIG. 11A is a diagram showing a modification of the marker that serves as the state recognizing portion of the manipulator system in FIG. 10A.
Figure 11B:
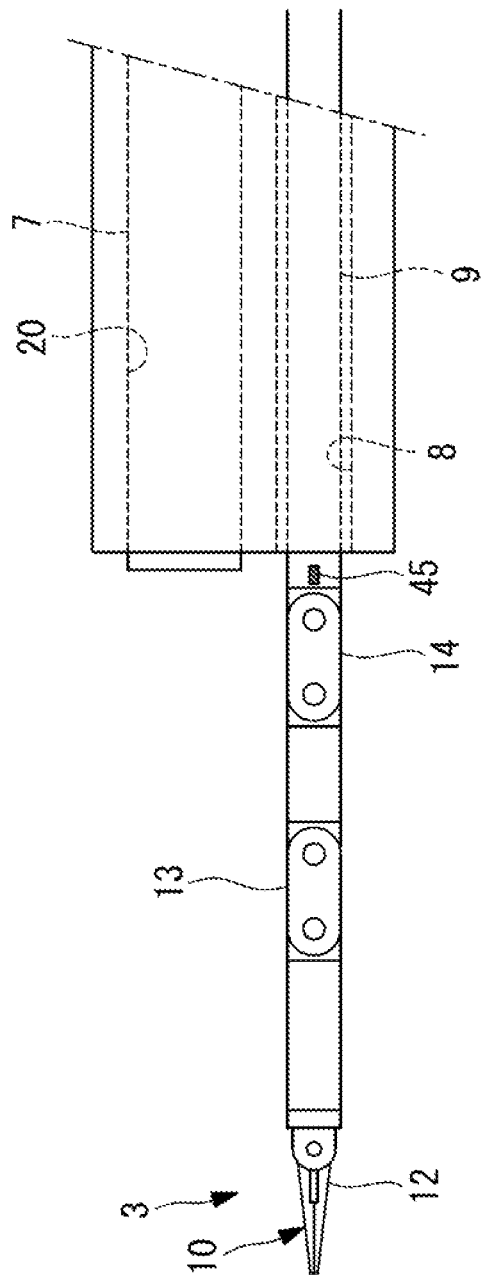
FIG. 11B is a diagram showing a state in which the marker is placed in the center by rotating the manipulator about a longitudinal axis of a flexible portion starting from the state in FIG. 11A.

In addition, although it is assumed that the operator O recognizes, by means of the marker 45 that appear in the endoscope image, the fact that the entire movable portion 10 has been made to protrude from the distal end of the manipulator channel 8, in addition, the rotation of the movable portion 10 about the longitudinal axis of the flexible portion 9 may also be initialized by using the marker 45. For example, as shown in FIGS. 11A and 11B, by employing marker that can be identified at circumferential-direction position as the marker 45, for example, marker 45 that exists only partially in the circumferential direction, as shown in FIG. 11B, the rotational position of the movable portion 10 may be adjusted so that the marker 45 appears on the front side in the endoscope image.

Figure 12:
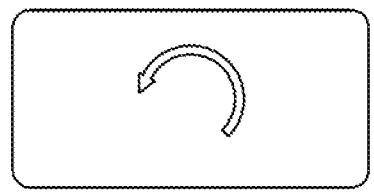
FIG. 12 is a diagram showing an example of a GUI screen for prompting a user to execute a rotational motion in FIG. 11B.
Figure 12:
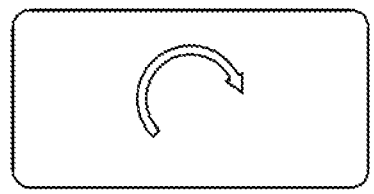
Figure 12:

In the case in which the manipulator 3 has a rotating joint on the proximal end side of the movable portion 10, buttons such as those shown in FIG. 12 may be displayed in the GUI, and the operator O may execute rotational manipulations and confirmation manipulation by using the buttons. The confirmation manipulation in this case may be shared with the confirmation manipulation for initializing the encoder 43.

In addition, instead of having the operator O recognize the fact that the entire movable portion 10 has been made to protrude from the distal end of the manipulator channel 8 and input this information via the input portion, the control portion 4 may be provided with: a shape estimating portion (not shown) that estimates a bent shape of the overtube 6; and a reciprocating-amount calculating portion (not shown) that calculates, on the basis of the estimated bent shape, the reciprocating amount of the driving portion 11 and the rotation amount thereof in the longitudinal direction that cause the entire movable portion 10 to be in the state of being protruded from the distal end of the manipulator channel 8.

Figure 13:
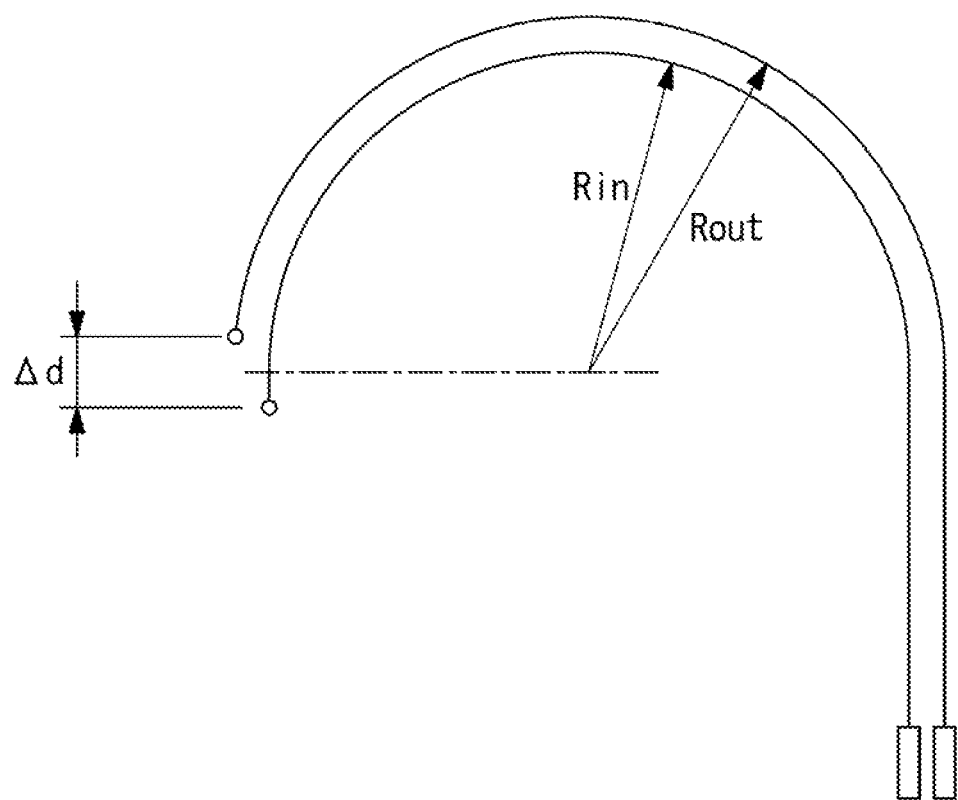
FIG. 13 is a diagram for explaining a calculation method of calculating, on the basis of a bent shape of the overtube, a reciprocating amount of the driving portion that causes the entire movable portion to be in the state of being protruded from the distal end of the manipulator channel.

The method of performing the calculation on the basis of the bent shape can be described by FIG. 13 and Expression (1).

$$\Delta d = \pi \times (R_{OUT} - R_{IN}) \times \theta / 180 \tag{1}$$

In addition, the control portion 4 may store identification information of a site-to-be-treated and a bent shape in a storage portion in association with each other, and may calculate the reciprocating amount of the driving portion 11 and the rotation amount thereof in the longitudinal direction on the basis of the bent shape read out from the storage portion when the operator O inputs, before performing treatment, the identification information of the site-to-be-treated.

In addition, the overtube 6 may be provided with a shape sensor (not shown) such as a strain gauge, an optical-fiber sensor, a magnetic sensor, or the like, and the reciprocating amount of the driving portion 11 and the rotation amount thereof in the longitudinal direction that cause the entire movable portion 10 to be protruded from the distal end of the manipulator channel 8 may be calculated on the basis of the bent shape of the overtube 6 detected by the shape sensor.

Figure 14:
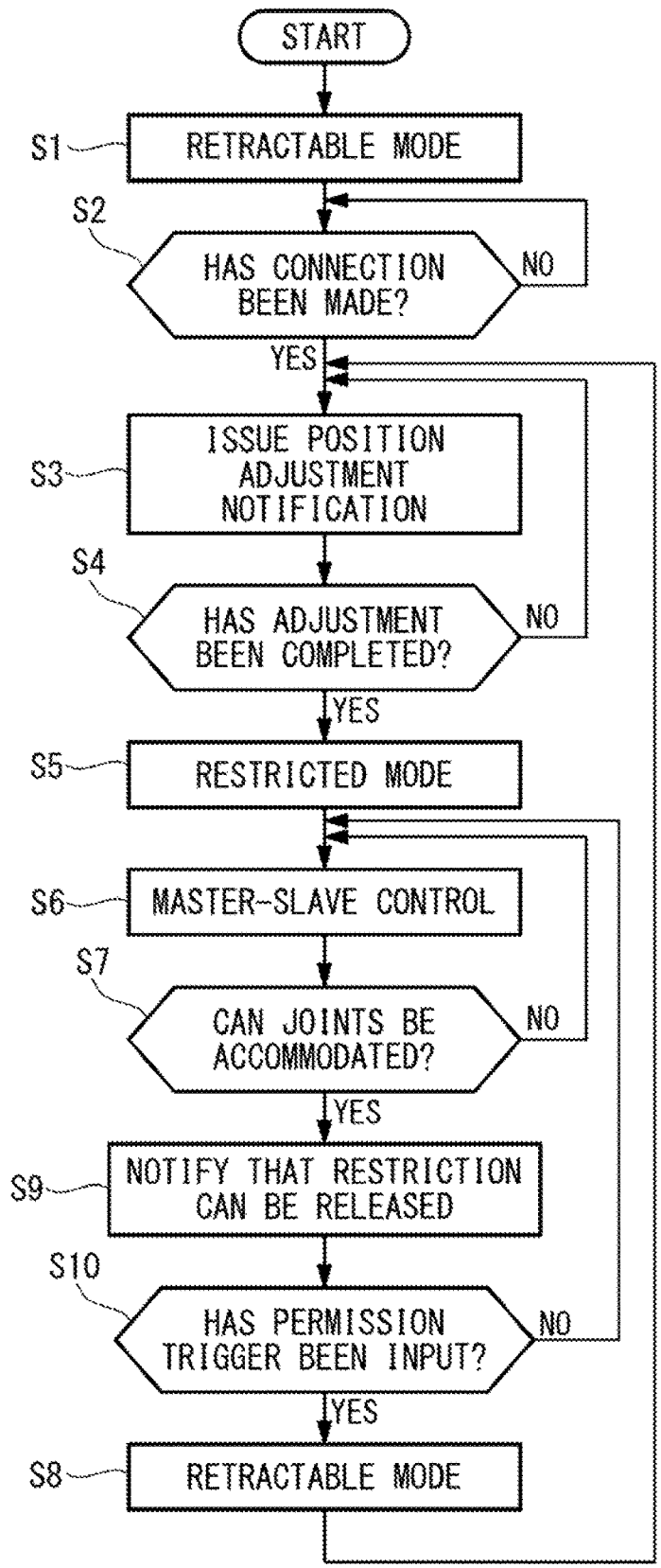
FIG. 14 is a flowchart showing a modification of the manipulator-system operating method in FIG. 9.

In addition, in this embodiment, although it is assumed that the control portion 4 releases the restriction by the brake 44 when the movable portion 10 takes a shape that allows accommodation thereof, alternatively, as shown in FIG. 14, the control portion (notifying portion) 4 may issue a notification about the fact that the restriction can be released when the movable portion 10 take the shape that allows accommodation thereof (step S9), and the restriction by the brake 44 may be released when the operator O presses a retraction permission trigger in the state in which the notification is being issued (step S10).

Figure 15:
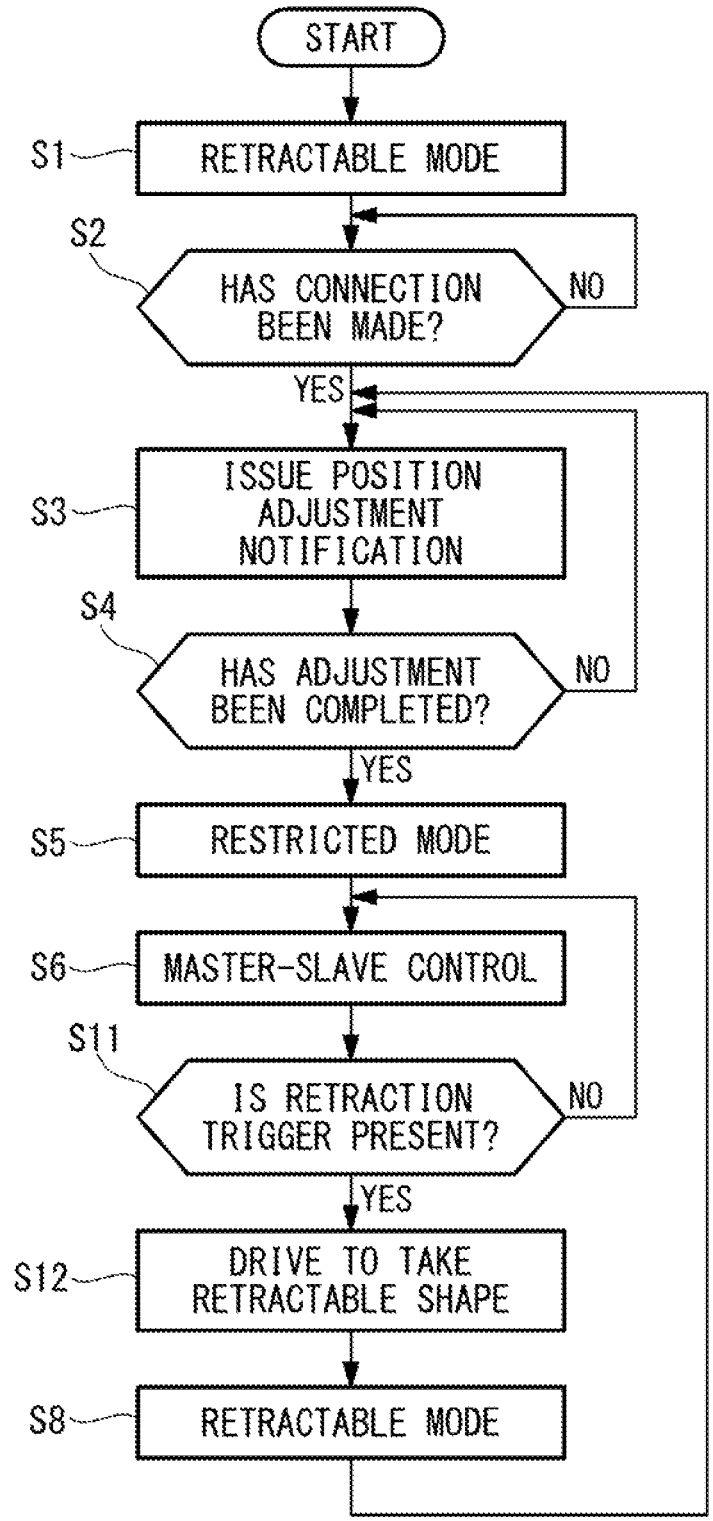
FIG. 15 is a flowchart showing another modification of the manipulator-system operating method in FIG. 9.

In addition, as shown in FIG. 15, n the restricted mode, in which the retraction toward the proximal end beyond the initial position is restricted by the brake 44, when the operator O presses the retraction trigger (step S11), the control portion 4 may control the movable portion 10 so as to be automatically driven to take a retractable shape (step S12), thus achieving the transition to the retractable mode. Then, after driving the movable portion 10 so as to take the retractable shape, the control portion 4 may move the slider 19 of the reciprocating mechanism 17 to the position on the most proximal-end side.

In addition, only while the operator O s holding the retraction trigger down, the control portion 4 may control the movable portion 10 so as to automatically be driven to take the retractable shape. In this case, when the operator O releases his/her hand from the retraction trigger, the control portion 4 stops the motion of the movable portion 10.

In addition, the operator O may release the restriction by the brake 44 in the case in which the disconnection between the motor unit 16 and the driving portion 11 is detected. When the connection between the motor unit 16 and the driving portion 11 is released, because the movable portion 10 is in a state in which the movable portion 10 is displaced in accordance with an external force, it is possible to remove the movable portion 10 from the channel 8 of the overtube 6 if the brake 44 has been released.

In addition, instead of achieving the transition to the retractable mode by means of the retraction trigger, the transition to the retractable mode may be achieved in the case in which a request for adjusting the position of the overtube 6 is detected.

In addition, although the case in which the channel 8 into which the manipulator 3 is inserted is provided in the overtube 6 has been described, the present invention may be applied to the case in which the manipulator 3 is introduced via a channel provided in the inserted portion of the endoscope 7.

The above-described embodiment leads to the following invention.

An aspect of the present invention is a manipulator system including: a manipulator that is provided with an elongated flexible portion, a movable portion provided at a distal end of the flexible portion, and a driving portion that is provided at a proximal end of the flexible portion and that drives the movable portion; an inserted portion that includes a channel through which the manipulator is made to pass and that possesses flexibility; a reciprocating portion that moves the driving portion forward and backward in a longitudinal direction of the flexible portion, thus causing the movable portion to be protruded from and retracted into a distal end of the channel; a movable-portion-state identifying portion that identifies a state of the movable portion; a restricting portion that, when the movable-portion-state identifying portion identifies the movable portion to be in a protruded state in which the entire movable portion is made to protrude from the distal end of the channel, restricts the driving portion from being moved backward any farther by the reciprocating portion; and a restriction releasing portion that, when the movable-portion-state identifying portion identifies the movable portion to be in a retractable state in which retraction thereof into the channel is possible, releases the restriction by the restricting portion.

With this aspect, by inserting the inserted portion possessing flexibility into, for example, the body of a patient while bending the inserted portion, the distal end thereof is placed at a position opposing an affected portion, by subsequently moving the reciprocating portion to which the driving portion is attached forward, the manipulator is moved forward via the channel of the inserted portion, and thus, the movable portion provided at the distal end thereof is made to protrude from the distal end of the channel. When the movable-portion-state identifying portion identifies the movable portion to be in a state in which the entirety thereof is made to protrude from the distal end of the channel, the operation of the restricting portion restricts the reciprocating portion so that the driving portion is not moved backward from that position.

In other words, because the movable portion is prevented from partially being retraced into the channel after the restriction by the restricting portion is in effect, the operator can freely operate, without limitation, the movable portion in a state in which the entirety thereof is made to protrude from the distal end of the channel. By doing so, it is possible to prevent the movable portion from being retracted into the channel in a bent state or the operator from unintentionally limiting the motion of the movable portion itself as a result of the movable portion being partially retracted into the channel.

In addition, when the movable-portion-state identifying portion identifies the movable portion to be in the state in which retraction thereof into the channel is possible, the restriction releasing portion releases the restriction by the restricting portion. By doing so, it is possible to smoothly retract the movable portion into the channel.

In the above-described aspect, the movable-portion-state identifying portion may identify the movable portion to be in the retractable state in which retraction thereof into the channel is possible when the movable portion takes a shape that is along the longitudinal direction of the flexible portion.

By doing so, because the movable-portion-state identifying portion identifies the movable portion to be in the retractable state when the operator causes the movable portion to take a shape that is along the longitudinal direction of the flexible portion, the restriction by the restricting portion is released by the restriction releasing portion, and thus, it is possible to smoothly retract the movable portion into the channel.

In addition, in the above-described aspect, the movable-portion-state identifying portion may be provided with a notifying portion that issues a notification about the fact that the movable portion can be retracted when the movable portion takes a shape that is along the longitudinal direction of the flexible portion, and an input portion with which a retraction instruction is input, and wherein the movable-portion-state identifying portion may identify the movable portion to be in the retractable state when the retraction instruction is input via the input portion in the state in which the notification about the fact that the retraction is possible is being issued by the notifying portion.

By doing so, because the notifying portion issues a notification about the fact that the movable portion is in the retractable state when the movable portion takes the shape that is along the longitudinal direction of the flexible portion, the operator can recognize the fact that the movable portion is in the retractable state. Then, when the operator who has recognized the fact that the movable portion is in the retractable state inputs a retraction instruction via the input portion, the movable-portion-state identifying portion identifies the movable portion to be in the retractable state, the restriction by the restricting portion is released, and thus, the operator can retract the movable portion into the channel.

In addition, the above-described aspect may be provided with: an input portion with which the retraction instruction is input; and a control portion that, when the retraction instruction is input via the input portion, drives the movable portion to take a shape that is along the longitudinal direction of the flexible portion.

By doing so, because the control portion controls the movable portion so as to be driven to take the shape that is along the longitudinal direction of the flexible portion when the operator inputs the retraction instruction via the input portion, the retractable state is automatically achieved, the movable-portion-state identifying portion identifies the movable portion to be in the retractable state, and thus, the restriction by the restricting portion is released. By doing so, it is possible to smoothly retract the movable portion into the channel.

In addition, the above-described aspect may be provided with: an input portion with which the retraction instruction is input; and a control portion that, in the state in which the retraction instruction has been input via the input portion, drives the movable portion to take a shape that is along the longitudinal direction of the flexible portion.

By doing so, because the control portion controls the movable portion so as to be driven to take the shape that is along the longitudinal direction of the flexible portion in the state in which the operator has input the retraction instruction via the input portion, the movable portion automatically approaches the retractable state so long as the retraction instruction is continued to be input, and, the motion of the movable portion is stopped when the input of the retraction instruction is stopped. By doing so, the movable portion is semi-automatically controlled under the management of the operator, and the restriction by the restricting portion is released when the retractable state is achieved.

In addition, another aspect of the present invention is a manipulator-system operating method including: a movable-portion-state identifying step of, in a state in which a manipulator provided with a movable portion at a distal end of an elongated flexible portion and a driving portion that drives the movable portion at a proximal end is inserted into a channel of an inserted portion that possesses flexibility and a bent shape thereof is set, identifying a state of the movable portion; a restricting step of, when the movable portion is identified to be in a protruded state in which the entire movable portion is made to protrude from a distal end of the channel in the movable-portion-state identifying step, restricting the driving portion from being moved backward from that position; and a restriction releasing step of, in the state in which the backward movement is restricted in the restricting step, releasing the restriction when the movable portion is identified to be in a retractable state in which retraction thereof into the channel is possible in the movable-portion-state identifying step.

REFERENCE SIGN LIST 1 manipulator system
3 manipulator
4 control portion (movable-portion-state identifying portion, restriction releasing portion, notifying portion)
6 overtube (inserted portion)
7 endoscope (image-acquisition portion)
8 channel
9 flexible portion
10 movable portion
11 driving portion
17 reciprocating mechanism (reciprocating portion)
43 restricting portion
S3 movable-portion-state identifying step
S5 restricting step
S8 restriction releasing step

The invention claimed is:

1. A manipulator system comprising:
a manipulator comprising:
an elongated flexible portion;
a movable portion provided at a distal end of the flexible portion; and
a driving portion provided at a proximal end of the flexible portion, the driving portion configured to drive the movable portion;
an inserted portion that comprises a channel through which the manipulator is made to pass and that possesses flexibility;
a reciprocating portion configured to move the driving portion forward and backward in a longitudinal direction of the flexible portion so as to cause the movable portion to be protruded from a distal end of the channel;
a movable-portion-state identifying portion configured to identify a state of the movable portion;
a restricting portion configured to restrict the driving portion from being moved by the reciprocating portion in case that the movable-portion-state identifying portion identifies the movable portion to be in a protruded state in which an entirety of the movable portion is made to protrude from the distal end of the channel; and
a restriction releasing portion configured to release a restriction of the driving portion by the restricting portion in case that the movable-portion-state identifying portion identifies the movable portion to be in a retractable state in which retraction thereof into the channel is possible.

2. The manipulator system according to claim 1, wherein the movable-portion-state identifying portion is configured to identify the movable portion to be in the retractable state in which the traction thereof into the channel is possible when the movable portion takes a shape that is along the longitudinal direction of the flexible portion.

3. The manipulator system according to claim 1, wherein the movable-portion-state identifying portion comprises:
a notifying portion configured to notify about a fact that the movable portion can be retracted when the movable portion takes a shape that is along the longitudinal direction of the flexible portion; and
an input portion with which a retraction instruction is configured to be input, and
wherein the movable-portion-state identifying portion is configured to identify the movable portion to be in the retractable state when the retraction instruction is input via the input portion in a state in which a notification about a fact that the retraction is possible is being issued by the notifying portion.

4. The manipulator system according to claim 1, further comprising:
an input portion with which a retraction instruction is configured to be input; and
a control portion configured to drive the movable portion to take a shape that is along the longitudinal direction of the flexible portion when the retraction instruction is input via the input portion.

5. The manipulator system according to claim 1, further comprising:
an input portion with which a retraction instruction is configured to be input; and a control portion configured to drive the movable portion to take a shape that is along the longitudinal direction of the flexible portion in a state in which the retraction instruction has been input via the input portion.

6. A manipulator system operating method comprising:
identifying a state of a movable portion of a manipulator when the manipulator is inserted into a channel of an inserted portion;
restricting a driving portion from being moved backward in case that the movable portion is identified to be in a protruded state in which an entirety of the movable portion is made to protrude from a distal end of the channel;
releasing a restriction of the driving portion in case that the movable portion is identified to be in a retractable state in which retraction thereof into the channel is possible.

7. The manipulator system operating method according to claim 6, wherein the movable portion is identified to be in the retractable state when the movable portion takes a shape that is along a longitudinal direction of a flexible portion of the manipulator.

8. A manipulator system comprising:
a manipulator comprising:
an elongated flexible portion;
a movable portion provided at a distal end of the flexible portion; and
a driving portion provided at a proximal end of the flexible portion, the driving portion configured to drive the movable portion;
an inserted portion that comprises a channel through which the manipulator is made to pass and that possesses flexibility;
a slider configured to move the driving portion forward and backward in a longitudinal direction of the flexible portion so as to cause the movable portion to be protruded from a distal end of the channel; and
a control portion configured:
to identify a state of the movable portion;
to restrict a movement of the driving portion by the slider, in case that the control portion identifies the movable portion to be in a protruded state in which an entirety of the movable portion is made to protrude from the distal end of the channel; and
to release a restriction of the movement of the driving portion by the slider, in case that the control portion identifies the movable portion to be in a retractable state in which retraction thereof into the channel is possible.

9. The manipulator system according to claim 8, wherein the control portion is configured to identify the movable portion to be in the retractable state in which the retraction thereof into the channel is possible when the movable portion takes a shape that is along the longitudinal direction of the flexible portion.

10. The manipulator system according to claim 8, wherein the control portion is configured to notify about the fact that the movable portion can be retracted when the movable portion takes a shape that is along the longitudinal direction of the flexible portion.

11. The manipulator system according to claim 8, wherein the control portion is configured to drive the movable portion to take a shape that is along the longitudinal direction of the flexible portion in case that the control portion identifies the movable portion to be in a retractable state in which retraction thereof into the channel is possible.

* * * * *

UNITED STATES PATENT AND TRADEMARK OFFICE
CERTIFICATE OF CORRECTION

PATENT NO.        : 11,083,533 B2                                               Page 1 of 1
APPLICATION NO.   : 16/011163
DATED             : August 10, 2021
INVENTOR(S)       : Keigo Takahashi et al.

It is certified that error appears in the above-identified patent and that said Letters Patent is hereby corrected as shown below:

In the Claims

Column 14, Line 39, delete "which the traction thereof" and insert --which the retraction thereof--

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*